US008353933B2

(12) United States Patent
Triplett et al.

(10) Patent No.: US 8,353,933 B2
(45) Date of Patent: Jan. 15, 2013

(54) FACET JOINT REPLACEMENT

(75) Inventors: Daniel J. Triplett, Providence, UT (US); Joel R Helgerson, Providence, UT (US); Andrew R. Fauth, River Heights, UT (US); David M. Skinlo, North Logan, UT (US); E. Marlowe Goble, Logan, UT (US); Daniel E. Gerbec, Logan, UT (US)

(73) Assignee: GMEDelaware 2 LLC, Audubon, PA (US)

( * ) Notice: Subject to any disclaimer, the term of this patent is extended or adjusted under 35 U.S.C. 154(b) by 1001 days.

(21) Appl. No.: 12/104,726

(22) Filed: Apr. 17, 2008

(65) Prior Publication Data
US 2008/0275507 A1    Nov. 6, 2008

Related U.S. Application Data

(63) Continuation-in-part of application No. 11/972,158, filed on Jan. 10, 2008.

(60) Provisional application No. 60/884,233, filed on Jan. 10, 2007, provisional application No. 60/912,323, filed on Apr. 17, 2007, provisional application No. 60/950,012, filed on Jul. 16, 2007, provisional application No. 60/950,021, filed on Jul. 16, 2007, provisional application No. 60/950,031, filed on Jul. 16, 2007, provisional application No. 60/950,038, filed on Jul. 16, 2007, provisional application No. 60/957,505, filed on Aug. 23, 2007, provisional application No. 60/968,324, filed on Aug. 27, 2007, provisional application No. 60/968,925, filed on Aug. 30, 2007, provisional application No. 60/975,731, filed on Sep. 28, 2007, provisional application No. 60/984,434, filed on Nov. 1, 2007, provisional application No. 60/984,428, filed on Nov. 1, 2007, provisional application No. 60/984,594, filed on Nov. 1, 2007, provisional application No. 60/984,798, filed on Nov. 2, 2007, provisional application No. 60/984,814, filed on Nov. 2, 2007, provisional application No. 60/984,983, filed on Apr. 17, 2008, provisional application No. 61/014,344, filed on Dec. 17, 2007, provisional application No. 61/015,866, filed on Dec. 21, 2007, provisional application No. 61/015,876, filed on Dec. 21, 2007, provisional application No. 61/015,886, filed on Dec. 21, 2007, provisional application No. 61/015,840, filed on Dec. 21, 2007, provisional application No. 61/040,041, filed on Mar. 27, 2008, provisional application No. 61/042,896, filed on Apr. 7, 2008, provisional application No. 61/045,526, filed on Apr. 16, 2008, provisional application No. 61/023,927, filed on Jan. 28, 2008, provisional application No. 61/033,473, filed on Mar. 4, 2008.

(51) Int. Cl.
*A61B 17/70* (2006.01)
(52) U.S. Cl. ........................... 606/247; 606/278
(58) Field of Classification Search .................. 606/246, 606/248, 249, 250, 251, 252, 253, 254–264, 606/247, 313
See application file for complete search history.

(56) References Cited

U.S. PATENT DOCUMENTS

| | | | |
|---|---|---|---|
| 2,677,369 | A | 5/1954 | Knowles |
| 3,247,000 | A | 4/1966 | Taylor |
| 3,298,372 | A | 1/1967 | Feinberg et al. |
| 3,426,364 | A | 2/1969 | Lumb |
| 3,486,505 | A | 12/1969 | Morrison |
| 3,508,954 | A | 4/1970 | White et al. |
| 3,648,691 | A | 3/1972 | Lumb et al. |
| 3,857,642 | A | 12/1974 | Miller |
| 3,867,728 | A | 2/1975 | Stubstad et al. |
| 3,875,595 | A | 4/1975 | Froning |
| 4,003,376 | A | 1/1977 | McKay et al. |
| 4,092,078 | A | 5/1978 | Klotz et al. |
| 4,289,123 | A | 9/1981 | Dunn |
| 4,349,921 | A | 9/1982 | Kuntz |
| 4,369,769 | A | 1/1983 | Edwards |
| 4,479,491 | A | 10/1984 | Martin |
| 4,483,334 | A | 11/1984 | Murray |
| 4,501,269 | A | 2/1985 | Bagby |

| | | | | | | |
|---|---|---|---|---|---|---|
| 4,554,914 A | 11/1985 | Kapp et al. | | 5,531,747 A | 7/1996 | Ray |
| 4,599,086 A | 7/1986 | Doty | | 5,534,028 A | 7/1996 | Bao et al. |
| 4,604,995 A | 8/1986 | Stephens et al. | | 5,534,030 A | 7/1996 | Navarro et al. |
| 4,611,581 A | 9/1986 | Steffee | | 5,534,031 A | 7/1996 | Matsuzaki et al. |
| 4,641,636 A | 2/1987 | Cotrel | | 5,540,688 A | 7/1996 | Navas |
| 4,653,481 A | 3/1987 | Howland et al. | | 5,545,166 A | 8/1996 | Howland |
| 4,657,550 A | 4/1987 | Daher | | 5,545,229 A | 8/1996 | Parsons et al. |
| 4,696,290 A | 9/1987 | Steffee | | 5,549,607 A | 8/1996 | Olson et al. |
| 4,743,260 A | 5/1988 | Burton | | 5,556,431 A | 9/1996 | Buttner-Janz |
| 4,759,769 A | 7/1988 | Hedman et al. | | 5,556,687 A | 9/1996 | McMillin |
| 4,772,287 A | 9/1988 | Ray et al. | | 5,562,735 A | 10/1996 | Margulies |
| 4,790,303 A | 12/1988 | Steffee | | 5,562,736 A | 10/1996 | Ray et al. |
| 4,800,874 A | 1/1989 | David et al. | | 5,562,737 A | 10/1996 | Graf |
| 4,805,602 A | 2/1989 | Puno et al. | | 5,569,248 A | 10/1996 | Mathews |
| 4,827,918 A | 5/1989 | Olerud | | 5,571,189 A | 11/1996 | Kuslich |
| 4,863,476 A | 9/1989 | Shepperd | | 5,571,191 A | 11/1996 | Fitz |
| 4,863,477 A | 9/1989 | Monson | | 5,572,191 A | 11/1996 | Lundberg |
| 4,892,545 A | 1/1990 | Day et al. | | 5,582,612 A | 12/1996 | Lin |
| 4,904,260 A | 2/1990 | Ray et al. | | 5,584,832 A | 12/1996 | Schlapfer |
| 4,911,718 A | 3/1990 | Lee et al. | | 5,603,713 A | 2/1997 | Aust et al. |
| 4,946,458 A | 8/1990 | Harms et al. | | 5,609,634 A | 3/1997 | Voydeville |
| 4,955,908 A | 9/1990 | Frey et al. | | 5,645,597 A | 7/1997 | Krapiva |
| 5,011,484 A | 4/1991 | Breard | | 5,645,599 A | 7/1997 | Samani |
| 5,015,255 A | 5/1991 | Kuslich | | 5,649,926 A | 7/1997 | Howland |
| 5,047,055 A | 9/1991 | Bao et al. | | 5,653,762 A | 8/1997 | Pisharodi |
| 5,071,437 A | 12/1991 | Steffee | | 5,666,243 A | 9/1997 | Brent |
| 5,092,866 A | 3/1992 | Breard et al. | | 5,672,175 A | 9/1997 | Martin |
| 5,092,867 A | 3/1992 | Harms et al. | | 5,674,295 A | 10/1997 | Ray et al. |
| 5,092,893 A | 3/1992 | Smith | | 5,674,296 A | 10/1997 | Bryan |
| 5,127,912 A | 7/1992 | Ray et al. | | 5,676,701 A | 10/1997 | Yuan et al. |
| 5,129,900 A | 7/1992 | Asher et al. | | 5,681,310 A | 10/1997 | Yuan et al. |
| 5,147,361 A | 9/1992 | Ojima et al. | | 5,683,464 A | 11/1997 | Wagner et al. |
| 5,147,404 A | 9/1992 | Downey | | 5,683,465 A | 11/1997 | Shinn et al. |
| 5,171,279 A | 12/1992 | Mathews | | 5,688,272 A | 11/1997 | Montague et al. |
| 5,171,280 A | 12/1992 | Baumgartner | | 5,690,629 A | 11/1997 | Asher et al. |
| 5,176,680 A * | 1/1993 | Vignaud et al. ............... 606/302 | | 5,702,392 A | 12/1997 | Wu et al. |
| 5,180,393 A | 1/1993 | Commarmond | | 5,702,450 A | 12/1997 | Bisserie |
| 5,192,326 A | 3/1993 | Bao et al. | | 5,702,453 A | 12/1997 | Rabbe et al. |
| 5,236,460 A | 8/1993 | Barber | | 5,704,936 A | 1/1998 | Mazel |
| 5,246,458 A | 9/1993 | Graham | | 5,713,900 A | 2/1998 | Benzel et al. |
| 5,258,031 A | 11/1993 | Salib et al. | | 5,716,415 A | 2/1998 | Steffee |
| 5,261,910 A | 11/1993 | Warden et al. | | 5,725,582 A | 3/1998 | Bevan et al. |
| 5,263,953 A | 11/1993 | Bagby | | 5,728,097 A | 3/1998 | Mathews |
| 5,282,863 A | 2/1994 | Burton | | 5,735,899 A | 4/1998 | Schwartz et al. |
| 5,304,178 A | 4/1994 | Stahurski | | 5,749,873 A | 5/1998 | Fairley |
| 5,306,275 A | 4/1994 | Bryan | | 5,755,796 A | 5/1998 | Ibo et al. |
| 5,306,308 A | 4/1994 | Gross et al. | | 5,772,661 A | 6/1998 | Michelson |
| 5,306,309 A | 4/1994 | Wagner et al. | | 5,797,909 A | 8/1998 | Michelson |
| 5,313,962 A | 5/1994 | Obenchain | | 5,814,046 A | 9/1998 | Hopf |
| 5,318,567 A | 6/1994 | Vichard | | 5,824,093 A | 10/1998 | Ray et al. |
| 5,360,430 A | 11/1994 | Lin | | 5,824,094 A | 10/1998 | Serhan et al. |
| 5,366,455 A | 11/1994 | Dove et al. | | 5,836,948 A | 11/1998 | Zucherman et al. |
| 5,370,697 A | 12/1994 | Baumgartner | | 5,860,977 A | 1/1999 | Zucherman et al. |
| 5,375,823 A | 12/1994 | Navas | | 5,865,846 A | 2/1999 | Bryan et al. |
| 5,387,213 A | 2/1995 | Breard et al. | | 5,868,745 A | 2/1999 | Alleyne |
| 5,391,168 A | 2/1995 | Sanders et al. | | 5,876,404 A | 3/1999 | Zucherman et al. |
| 5,401,269 A | 3/1995 | Buttner-Janz et al. | | 5,888,223 A | 3/1999 | Bray, Jr. |
| 5,415,661 A | 5/1995 | Holmes | | 5,893,889 A | 4/1999 | Harrington |
| 5,437,669 A | 8/1995 | Yuan et al. | | RE36,221 E | 6/1999 | Breard et al. |
| 5,437,672 A | 8/1995 | Alleyne | | 5,916,267 A | 6/1999 | Tienboon |
| 5,439,464 A | 8/1995 | Shapiro | | 5,951,555 A | 9/1999 | Rehak et al. |
| 5,443,516 A | 8/1995 | Albrektsson et al. | | 5,961,516 A | 10/1999 | Graf |
| 5,456,722 A | 10/1995 | McLeod et al. | | 5,986,169 A | 11/1999 | Gjunter |
| 5,458,641 A | 10/1995 | Ramirez Jimenez | | 6,001,130 A | 12/1999 | Bryan et al. |
| 5,458,642 A | 10/1995 | Beer et al. | | 6,004,322 A | 12/1999 | Bernstein |
| 5,458,643 A | 10/1995 | Oka et al. | | 6,014,588 A | 1/2000 | Fitz |
| 5,464,439 A | 11/1995 | Gendler | | 6,019,759 A | 2/2000 | Rogozinski |
| 5,466,237 A | 11/1995 | Byrd | | 6,019,792 A | 2/2000 | Cauthen |
| 5,470,333 A | 11/1995 | Ray | | 6,039,761 A | 3/2000 | Li et al. |
| 5,476,463 A | 12/1995 | Boachie-Adjei et al. | | 6,039,763 A | 3/2000 | Shelokov |
| 5,480,401 A | 1/1996 | Navas | | 6,048,342 A | 4/2000 | Zucherman et al. |
| 5,489,308 A | 2/1996 | Kuslich et al. | | 6,063,088 A | 5/2000 | Winslow |
| 5,496,318 A | 3/1996 | Howland et al. | | 6,063,121 A | 5/2000 | Xavier et al. |
| 5,507,745 A | 4/1996 | Logroscino et al. | | 6,066,325 A | 5/2000 | Wallace et al. |
| 5,507,813 A | 4/1996 | Dowd et al. | | 6,068,630 A | 5/2000 | Zucherman et al. |
| 5,514,180 A | 5/1996 | Heggeness et al. | | RE36,758 E | 6/2000 | Fitz |
| 5,522,899 A | 6/1996 | Michelson | | 6,074,390 A | 6/2000 | Zucherman et al. |
| 5,527,312 A | 6/1996 | Ray | | 6,080,157 A | 6/2000 | Cathro et al. |
| 5,531,745 A | 7/1996 | Ray | | 6,090,112 A | 7/2000 | Zucherman et al. |

| | | | | | | |
|---|---|---|---|---|---|---|
| 6,093,205 | A | 7/2000 | McLeod et al. | 7,087,084 B2 | 8/2006 | Reiley |
| 6,113,637 | A | 9/2000 | Gill et al. | 2001/0007073 A1 | 7/2001 | Zucherman et al. |
| 6,113,639 | A | 9/2000 | Ray et al. | 2001/0012938 A1 | 8/2001 | Zucherman et al. |
| 6,132,464 | A | 10/2000 | Martin | 2001/0016743 A1 | 8/2001 | Zucherman et al. |
| 6,132,465 | A | 10/2000 | Ray et al. | 2001/0021850 A1 | 9/2001 | Zucherman et al. |
| 6,146,421 | A | 11/2000 | Gordon et al. | 2001/0031965 A1 | 10/2001 | Zucherman et al. |
| 6,149,652 | A | 11/2000 | Zucherman et al. | 2001/0039452 A1 | 11/2001 | Zucherman et al. |
| 6,151,934 | A | 11/2000 | Chong et al. | 2002/0029039 A1 | 3/2002 | Zucherman et al. |
| 6,152,926 | A | 11/2000 | Zucherman et al. | 2002/0065557 A1 | 5/2002 | Goble et al. |
| 6,156,038 | A | 12/2000 | Zucherman et al. | 2002/0072800 A1 | 6/2002 | Goble et al. |
| 6,156,067 | A | 12/2000 | Bryan et al. | 2002/0091446 A1 | 7/2002 | Zucherman et al. |
| 6,176,861 | B1 | 1/2001 | Bernstein et al. | 2002/0099384 A1 | 7/2002 | Scribner et al. |
| 6,179,838 | B1 | 1/2001 | Fiz | 2002/0116000 A1 | 8/2002 | Zucherman et al. |
| 6,183,471 | B1 | 2/2001 | Zucherman et al. | 2002/0123806 A1 | 9/2002 | Reiley |
| 6,187,005 | B1 * | 2/2001 | Brace et al. ................. 606/264 | 2002/0143331 A1 | 10/2002 | Zucherman et al. |
| 6,190,387 | B1 | 2/2001 | Zucherman et al. | 2002/0151895 A1 | 10/2002 | Soboleski et al. |
| 6,190,414 | B1 | 2/2001 | Young et al. | 2002/0183746 A1 | 12/2002 | Zucherman et al. |
| 6,206,882 | B1 | 3/2001 | Cohen | 2003/0004572 A1 | 1/2003 | Goble et al. |
| 6,206,922 | B1 | 3/2001 | Zdeblick et al. | 2003/0009226 A1 | 1/2003 | Graf |
| 6,228,118 | B1 | 5/2001 | Gordon | 2003/0028250 A1 | 2/2003 | Reiley et al. |
| 6,235,030 | B1 | 5/2001 | Zucherman et al. | 2003/0040797 A1 | 2/2003 | Fallin et al. |
| 6,238,397 | B1 | 5/2001 | Zucherman et al. | 2003/0055427 A1 | 3/2003 | Graf |
| 6,241,730 | B1 | 6/2001 | Alby | 2003/0065330 A1 | 4/2003 | Zucherman et al. |
| 6,264,655 | B1 | 7/2001 | Pisharodi | 2003/0073998 A1 | 4/2003 | Pagliuca et al. |
| 6,267,764 | B1 | 7/2001 | Elberg | 2003/0109880 A1 | 6/2003 | Shirado et al. |
| 6,280,444 | B1 | 8/2001 | Zucherman et al. | 2003/0153912 A1 | 8/2003 | Graf |
| 6,290,700 | B1 | 9/2001 | Schmotzer | 2003/0191470 A1 | 10/2003 | Ritland |
| 6,293,949 | B1 | 9/2001 | Justis et al. | 2003/0220642 A1 | 11/2003 | Freudiger |
| 6,312,469 | B1 | 11/2001 | Gielen et al. | 2003/0220643 A1 | 11/2003 | Ferree |
| 6,314,325 | B1 | 11/2001 | Fitz | 2004/0006341 A1 | 1/2004 | Shaolian et al. |
| 6,332,882 | B1 | 12/2001 | Zucherman et al. | 2004/0006391 A1 | 1/2004 | Reiley |
| 6,332,883 | B1 | 12/2001 | Zucherman et al. | 2004/0024458 A1 | 2/2004 | Senegas et al. |
| 6,379,355 | B1 | 4/2002 | Zucherman et al. | 2004/0049189 A1 | 3/2004 | Le Couedic et al. |
| 6,402,750 | B1 | 6/2002 | Atkinson et al. | 2004/0049190 A1 | 3/2004 | Biedermann et al. |
| 6,413,259 | B1 | 7/2002 | Lyons et al. | 2004/0049272 A1 | 3/2004 | Reiley |
| 6,419,676 | B1 | 7/2002 | Zucherman et al. | 2004/0049273 A1 | 3/2004 | Reiley |
| 6,419,677 | B2 | 7/2002 | Zucherman et al. | 2004/0049274 A1 | 3/2004 | Reiley |
| 6,419,703 | B1 | 7/2002 | Fallin et al. | 2004/0049275 A1 | 3/2004 | Reiley |
| 6,419,704 | B1 | 7/2002 | Ferree | 2004/0049276 A1 | 3/2004 | Reiley |
| 6,440,169 | B1 | 8/2002 | Elberg et al. | 2004/0049277 A1 | 3/2004 | Reiley |
| 6,447,546 | B1 | 9/2002 | Bramlet et al. | 2004/0049278 A1 | 3/2004 | Reiley |
| 6,451,019 | B1 | 9/2002 | Zucherman et al. | 2004/0049281 A1 | 3/2004 | Reiley |
| 6,451,020 | B1 | 9/2002 | Zucherman et al. | 2004/0059331 A1 | 3/2004 | Mullaney |
| 6,458,131 | B1 | 10/2002 | Ray | 2004/0073215 A1 | 4/2004 | Carli |
| 6,461,359 | B1 | 10/2002 | Tribus et al. | 2004/0078082 A1 | 4/2004 | Lange |
| 6,471,704 | B2 | 10/2002 | Gertzbein et al. | 2004/0082954 A1 | 4/2004 | Teitelbaum et al. |
| 6,475,219 | B1 | 11/2002 | Shelokov | 2004/0087950 A1 | 5/2004 | Teitelbaum |
| 6,478,796 | B2 | 11/2002 | Zucherman et al. | 2004/0106995 A1 | 6/2004 | Le Couedic et al. |
| 6,481,440 | B2 | 11/2002 | Gielen et al. | 2004/0111154 A1 | 6/2004 | Reiley |
| 6,485,518 | B1 | 11/2002 | Cornwall et al. | 2004/0116927 A1 | 6/2004 | Graf |
| 6,500,178 | B2 | 12/2002 | Zucherman et al. | 2004/0117017 A1 | 6/2004 | Pasquet et al. |
| 6,514,256 | B2 | 2/2003 | Zucherman et al. | 2004/0127989 A1 | 7/2004 | Dooris et al. |
| 6,527,806 | B2 | 3/2003 | Ralph et al. | 2004/0143264 A1 | 7/2004 | McAfee |
| 6,540,747 | B1 | 4/2003 | Marino | 2004/0147928 A1 | 7/2004 | Landry et al. |
| 6,540,785 | B1 | 4/2003 | Gill et al. | 2004/0153071 A1 | 8/2004 | Zucherman et al. |
| 6,565,605 | B2 | 5/2003 | Goble et al. | 2004/0158245 A1 | 8/2004 | Chin |
| 6,579,319 | B2 | 6/2003 | Goble et al. | 2004/0167520 A1 | 8/2004 | Zucherman et al. |
| 6,582,433 | B2 | 6/2003 | Yun | 2004/0172025 A1 | 9/2004 | Drewry et al. |
| 6,585,769 | B1 | 7/2003 | Muhanna et al. | 2004/0181282 A1 | 9/2004 | Zucherman et al. |
| 6,610,091 | B1 | 8/2003 | Reiley | 2004/0181285 A1 | 9/2004 | Simonson |
| 6,616,669 | B2 | 9/2003 | Ogilvie et al. | 2004/0186475 A1 | 9/2004 | Falahee |
| 6,626,909 | B2 | 9/2003 | Chin | 2004/0220568 A1 | 11/2004 | Zucherman et al. |
| 6,626,944 | B1 | 9/2003 | Taylor | 2004/0225289 A1 | 11/2004 | Biedermann et al. |
| 6,652,527 | B2 | 11/2003 | Zucherman et al. | 2004/0230192 A1 | 11/2004 | Graf |
| 6,652,534 | B2 | 11/2003 | Zucherman et al. | 2004/0230201 A1 | 11/2004 | Yuan et al. |
| 6,652,585 | B2 | 11/2003 | Lange | 2004/0230304 A1 | 11/2004 | Yuan et al. |
| 6,660,005 | B2 | 12/2003 | Toyama | 2004/0236327 A1 | 11/2004 | Paul et al. |
| 6,669,729 | B2 | 12/2003 | Chin | 2004/0236328 A1 | 11/2004 | Paul et al. |
| 6,695,842 | B2 | 2/2004 | Zucherman et al. | 2004/0236329 A1 | 11/2004 | Panjabi |
| 6,699,246 | B2 | 3/2004 | Zucherman et al. | 2004/0243239 A1 | 12/2004 | Taylor |
| 6,699,247 | B2 | 3/2004 | Zucherman et al. | 2005/0010291 A1 | 1/2005 | Stinson et al. |
| 6,733,534 | B2 | 5/2004 | Sherman | 2005/0010293 A1 | 1/2005 | Zucherman et al. |
| 6,761,719 | B2 | 7/2004 | Justis et al. | 2005/0010298 A1 | 1/2005 | Zucherman et al. |
| 6,761,720 | B1 | 7/2004 | Senegas | 2005/0027361 A1 | 2/2005 | Reiley |
| 6,783,527 | B2 | 8/2004 | Drewry et al. | 2005/0043797 A1 | 2/2005 | Lee |
| 6,796,983 | B1 | 9/2004 | Zucherman et al. | 2005/0055096 A1 | 3/2005 | Serham et al. |
| 6,811,567 | B2 | 11/2004 | Reiley | 2005/0070899 A1 | 3/2005 | Doubler |
| 6,835,205 | B2 | 12/2004 | Atkinson et al. | 2005/0119748 A1 * | 6/2005 | Reiley et al. ................. 623/17.11 |
| 6,835,207 | B2 | 12/2004 | Zacouto et al. | 2005/0131406 A1 * | 6/2005 | Reiley et al. ................. 606/61 |

| | | | | | | | |
|---|---|---|---|---|---|---|---|
| 2005/0131545 | A1* | 6/2005 | Chervitz et al. ............ 623/17.14 | WO | WO2004017817 | A2 | 3/2004 |
| 2005/0137705 | A1 | 6/2005 | Reiley | WO | WO2004019762 | A2 | 3/2004 |
| 2005/0137706 | A1 | 6/2005 | Reiley | WO | WO2004024010 | A1 | 3/2004 |
| 2005/0143818 | A1 | 6/2005 | Yuan et al. | WO | WO2004032794 | A2 | 4/2004 |
| 2005/0149190 | A1 | 7/2005 | Reiley | WO | WO2004032794 | A3 | 4/2004 |
| 2005/0154467 | A1 | 7/2005 | Peterman et al. | WO | WO2004039239 | A2 | 5/2004 |
| 2005/0177166 | A1* | 8/2005 | Timm et al. ................. 606/73 | WO | WO2004039239 | A3 | 5/2004 |
| 2005/0240265 | A1 | 10/2005 | Kuiper et al. | WO | WO2004039243 | A2 | 5/2004 |
| 2005/0240266 | A1* | 10/2005 | Kuiper et al. ............. 623/17.11 | WO | WO2004039243 | A3 | 5/2004 |
| 2006/0052785 | A1 | 3/2006 | Augostino et al. | WO | WO2004041066 | A2 | 5/2004 |
| 2006/0200149 | A1* | 9/2006 | Hoy et al. .................. 606/72 | WO | WO2004041066 | A3 | 5/2004 |
| 2006/0217718 | A1* | 9/2006 | Chervitz et al. ............. 606/61 | WO | WO2004073533 | A1 | 9/2004 |
| 2006/0282074 | A1 | 12/2006 | Renaud et al. | WO | WO2004098423 | A1 | 11/2004 |
| 2008/0275507 | A1* | 11/2008 | Triplett et al. ............... 606/278 | WO | WO2004098452 | A2 | 11/2004 |
| | | | | WO | WO2004105577 | A2 | 12/2004 |
| | | FOREIGN PATENT DOCUMENTS | | WO | WO2004105580 | A2 | 12/2004 |
| EP | | 408489 A1 | 1/1991 | WO | WO2005013864 | | 2/2005 |
| EP | | 322334 B1 | 2/1992 | WO | WO2005037149 | | 4/2005 |
| EP | | 667127 A1 | 8/1995 | WO | WO2005044152 | A1 | 5/2005 |
| EP | | 767637 B1 | 11/1998 | | | | |
| EP | | 768843 B1 | 2/1999 | | OTHER PUBLICATIONS | | |
| EP | | 669109 B1 | 5/1999 | | | | |
| EP | | 1239785 B1 | 9/2004 | | | | |
| EP | | 1343424 B1 | 9/2004 | | | | |
| EP | | 1399078 B1 | 12/2004 | | | | |
| FR | | 2721501 B1 | 8/1996 | | | | |
| JP | | 10179622 A2 | 7/1998 | | | | |
| JP | | 10277070 A2 | 10/1998 | | | | |
| SU | | 1468543 A1 | 3/1989 | | | | |
| SU | | 1517953 A1 | 10/1989 | | | | |
| WO | | WO8707827 A1 | 12/1987 | | | | |
| WO | | WO9421185 A1 | 9/1994 | | | | |
| WO | | WO9505783 A1 | 3/1995 | | | | |
| WO | | WO9505784 A1 | 3/1995 | | | | |
| WO | | WO9505785 A1 | 3/1995 | | | | |
| WO | | WO9505786 A1 | 3/1995 | | | | |
| WO | | WO9600049 A1 | 1/1996 | | | | |
| WO | | WO9822033 A1 | 5/1998 | | | | |
| WO | | WO9848707 A1 | 11/1998 | | | | |
| WO | | WO9848717 A1 | 11/1998 | | | | |
| WO | | WO9856301 A1 | 12/1998 | | | | |
| WO | | WO9905995 A1 | 2/1999 | | | | |
| WO | | WO9921500 A1 | 5/1999 | | | | |
| WO | | WO9921501 A1 | 5/1999 | | | | |
| WO | | WO9923963 A1 | 5/1999 | | | | |
| WO | | WO9965412 A1 | 12/1999 | | | | |
| WO | | WO9960957 A1 | 5/2000 | | | | |
| WO | | WO 0038582 | 7/2000 | | | | |
| WO | | WO0062684 A1 | 10/2000 | | | | |
| WO | | WO0130248 A1 | 5/2001 | | | | |
| WO | | WO0145576 A1 | 6/2001 | | | | |
| WO | | WO0149192 A1 | 7/2001 | | | | |
| WO | | WO0156489 A1 | 8/2001 | | | | |
| WO | | WO0164142 A1 | 9/2001 | | | | |
| WO | | WO0164144 A2 | 9/2001 | | | | |
| WO | | WO0191657 A1 | 12/2001 | | | | |
| WO | | WO0191658 A1 | 12/2001 | | | | |
| WO | | WO197721 A2 | 12/2001 | | | | |
| WO | | WO0197721 A3 | 12/2001 | | | | |
| WO | | WO0200124 A1 | 1/2002 | | | | |
| WO | | WO0203882 A2 | 1/2002 | | | | |
| WO | | WO0207621 A1 | 1/2002 | | | | |
| WO | | WO0207622 A1 | 1/2002 | | | | |
| WO | | WO0207623 A1 | 1/2002 | | | | |
| WO | | WO0213732 A2 | 2/2002 | | | | |
| WO | | WO0230336 A2 | 4/2002 | | | | |
| WO | | WO0234120 A2 | 5/2002 | | | | |
| WO | | WO0243603 A1 | 6/2002 | | | | |
| WO | | WO02067792 A2 | 9/2002 | | | | |
| WO | | WO02067793 A2 | 9/2002 | | | | |
| WO | | WO02089712 A1 | 11/2002 | | | | |
| WO | | WO02089712 A2 | 11/2002 | | | | |
| WO | | WO02102259 A2 | 12/2002 | | | | |
| WO | | WO03009737 A1 | 2/2003 | | | | |
| WO | | WO03011147 A1 | 2/2003 | | | | |
| WO | | WO03015646 A2 | 2/2003 | | | | |
| WO | | WO03045262 A2 | 6/2003 | | | | |
| WO | | WO03077806 A1 | 9/2003 | | | | |

Goh JC, et al., "Influence of PLIF cage size on lumbar spine stability", Spine, Jan. 2000 25:1, PubMed abstract.

Head WC, Wagner surface replacement arthroplasty of the hip. Analysis of fourteen failures om forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent amd distal facet force and lumbosacral motion", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

Todd Anres; *Facet Joint Arthroplasty: A Glimpse of the Future of Spine Technology*, Othopaedic Product News. Sep./Oct. 2005 p. 38, 40.

* cited by examiner

*Primary Examiner* — Alvin Stewart
*Assistant Examiner* — James Palmer

(57) ABSTRACT

A facet joint replacement system includes an inferior implant with an inferior articular surface, and a superior implant with a superior articular surface. The inferior implant may comprise an inferior strut, and a polyaxially adjustable, lockable mechanism which couples the inferior articular surface with a first end of the inferior strut. A second end of the inferior strut may be secured to a polyaxially adjustable, lockable fixation assembly securable in a vertebra. The first end of the inferior strut may be post-shaped, and the second end ring-shaped, and vice versa. The superior implant may be secured to a polyaxially adjustable lockable fixation assembly securable in a vertebra. Inferior and superior implants may be implanted individually, paired on one lateral vertebral side, bi-laterally, and/or in multiple vertebral levels. A crosslink may be secured to one implant and extend across a vertebral sagittal plane to a second implant. A clip may align the articular surfaces during implantation.

21 Claims, 23 Drawing Sheets

FACET JOINT REPLACEMENT

CROSS-REFERENCE TO RELATED APPLICATIONS

This application is a continuation-in-part of the following, which is incorporated herein by reference:

pending U.S. application Ser. No. 11/972,158, filed Jan. 10, 2008, and is entitled TAPER-LOCKING FIXATION SYSTEM, which claims the benefit of the following, which are also incorporated herein by reference:

pending U.S. Provisional Patent Application No. 60/884,233, filed Jan. 10, 2007, and is entitled TAPER-LOCKING ROD FIXATION SYSTEM;

pending U.S. Provisional Application No. 60/912,323, filed Apr. 17, 2007, and is entitled AFRS MULTI-LEVEL IMPLANT SYSTEM;

pending U.S. Provisional Application No. 60/950,012, filed Jul. 16, 2007, and is entitled INFERIOR FACET IMPLANT HOLDER;

pending U.S. Provisional Application No. 60/950,021, filed Jul. 16, 2007, and is entitled MONORAIL INSTRUMENT GUIDANCE SYSTEM FOR LUMBAR SPINAL SURGERY;

pending U.S. Provisional Application No. 60/950,031, filed Jul. 16, 2007, and is entitled LINEAR POLYAXIAL LOCKING MECHANISM WITH TOOL;

pending U.S. Provisional Application No. 60/950,038, filed Jul. 16, 2007, and is entitled MOBILE INFERIOR FACET BEARING WITH SUPERIOR CLIP;

pending U.S. Provisional Application No. 60/957,505, filed Aug. 23, 2007, and is entitled DYNAMIC STABILIZATION AND STATIC FIXATION OPTIONS FOR FACET REPLACEMENT PROSTHESIS;

pending U.S. Provisional Application No. 60/968,324, filed Aug. 27, 2007, and is entitled INTERVERTEBRAL DISC IMPLANT WITH FACET MOTION CONSTRAINTS;

pending U.S. Provisional Application No. 60/968,925, filed Aug. 30, 2007, and is entitled SYSTEMS AND METHODS FOR LESS INVASIVE FACET JOINT REPLACEMENT;

pending U.S. Provisional Application No. 60/975,731, filed Sep. 28, 2007, and is entitled MONOLITHIC INFERIOR IMPLANT STRUT WITH INTEGRAL CROSS LINK CLAMP;

pending U.S. Provisional Application No. 60/984,434, filed Nov. 1, 2007, and is entitled SUPERIOR INSTRUMENTS;

pending U.S. Provisional Application No. 60/984,428, filed Nov. 1, 2007, and is entitled CROSS LINK CLAMP;

pending U.S. Provisional Application No. 60/984,594, filed Nov. 1, 2007, and is entitled LOW PROFILE POLYAXIAL FACET IMPLANT;

pending U.S. Provisional Application No. 60/984,798, filed Nov. 2, 2007, and is entitled LOW PROFILE POLYAXIAL FACET IMPLANT;

pending U.S. Provisional Application No. 60/984,814, filed Nov. 2, 2007, and is entitled HINGED EYELET SCREW;

pending U.S. Provisional Application No. 60/984,983, filed Nov. 2, 2007, and is entitled ADJUSTABLE FACET IMPLANT BASE PIECE;

pending U.S. Provisional Application No. 61/014,344, filed Dec. 17, 2007, and is entitled INFERIOR STRUT UPDATE;

pending U.S. Provisional Application No. 61/015,866, filed Dec. 21, 2007, and is entitled INTERVERTEBRAL DISC IMPLANT WITH FACET MOTION CONSTRAINTS INCLUDING POSTERIOR COMBINATION;

pending U.S. Provisional Application No. 61/015,876, filed Dec. 21, 2007, and is entitled INTERVERTEBRAL DISC IMPLANT WITH FACET MOTION CONSTRAINTS AND METHODS FOR IMPLANT ALIGNMENT;

pending U.S. Provisional Application No. 61/015,886, filed Dec. 21, 2007, and is entitled EYELET PEDICLE SCREW WITH MULTI-AXIAL FIXATION; and pending U.S. Provisional Application No. 61/015,840, filed Dec. 21, 2007, and is entitled CERVICAL PLATE WITH FACET MOTION CONTROL.

This application also claims the benefit of the following, which are incorporated herein by reference:

pending U.S. Provisional Application No. 61/023,927, filed Jan. 28, 2008, and is entitled AFRS GENERATION II INSTRUMENTS;

pending U.S. Provisional Application No. 61/033,473, filed Mar. 4, 2008, and is entitled TOP LOADING RECEIVER FOR AN ADJUSTABLE FACET REPLACEMENT;

pending U.S. Provisional Application No. 61/040,041, filed Mar. 27, 2008, and is entitled FACET JOINT REPLACEMENT;

pending U.S. Provisional Application No. 61/042,896, filed Apr. 7, 2008, and is entitled SPINAL FIXATION ON AN IMPLANT BASE; and pending U.S. Provisional Application No. 61/045,526, filed Apr. 16, 2008, and is entitle INFERIOR BASE-SPLIT CLAMP AND MULTI-LEVEL SPLIT CLAMP.

BACKGROUND OF THE INVENTION

1. The Field of the Invention

The invention relates to spinal surgery. More specifically, the invention relates to replacement of natural vertebral facet joints with implantable artificial facet joint replacements.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to replace natural vertebral facet joints with implantable artificial facet joint prostheses in a manner that provides a high degree of implant adjustability, simplicity, and ease of use.

In this application, "polyaxial" rotation is rotation that can occur about at least two axes that are not parallel to each other. "Lock-out" between two or more component parts refers to a state in which movement of any component part is prevented by frictional, compression, expansion, or other forces. A "taper-lock connector" refers to any locking mechanism that uses a taper to effect locking.

Figure 1:
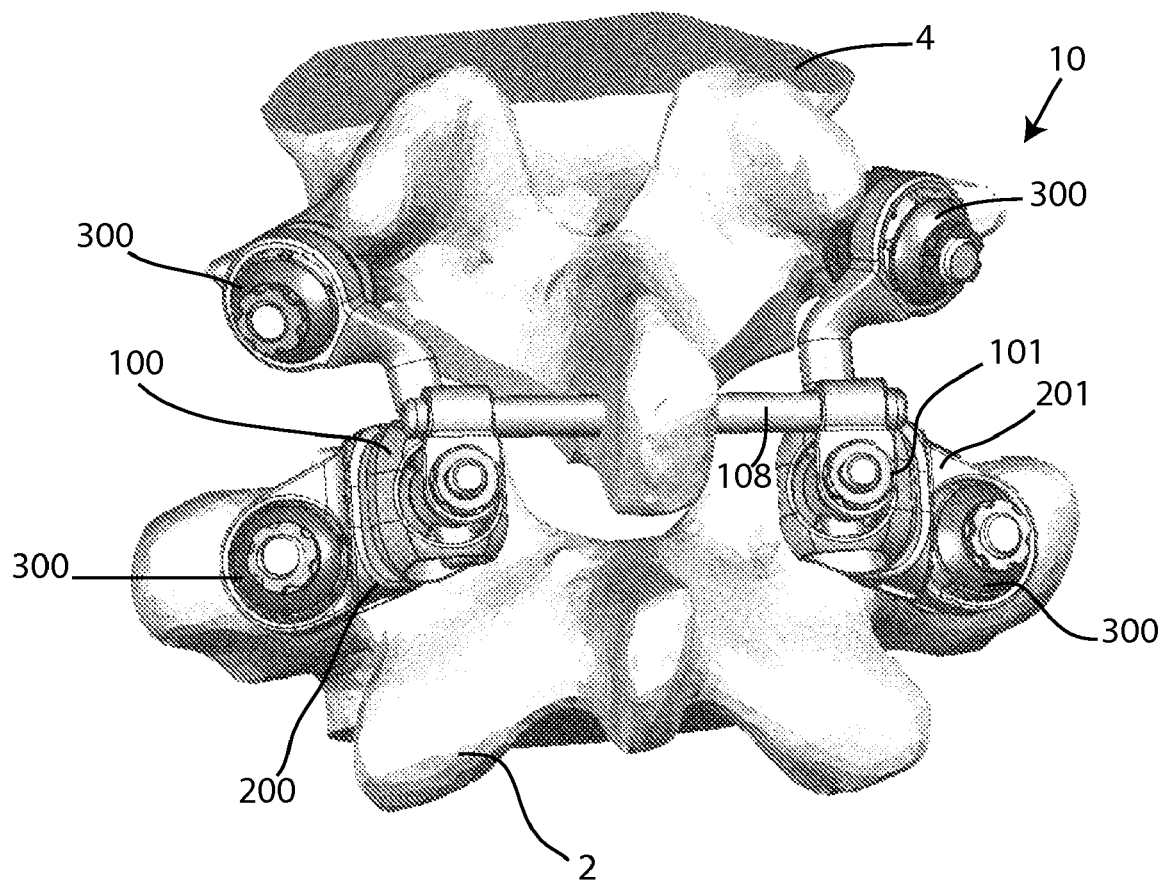
FIG. 1 is a perspective view of a portion of a spine with a bi-lateral facet joint replacement system implanted into two adjacent vertebrae.

Referring to FIG. 1, a perspective view depicts a portion of a spine including a first vertebra 2 and a second vertebra 4. A system 10 of bi-lateral facet joint replacements joined by a crosslink rod passing through a spinous process 6 is implanted in the vertebrae. On the left side of the vertebrae, an inferior facet joint implant 100 is secured to a fixation assembly 300 implanted in vertebra 4, and a superior facet joint implant 200 is secured to a fixation assembly 300 implanted in vertebra 2. On the right side of the vertebrae, an inferior facet joint implant 101 is secured to a fixation member 300 implanted in vertebra 4, and a superior facet joint implant 201 is secured to a fixation member 200 implant in vertebra 2. It is appreciated that the facet joint replacement implants described herein may each be configured in a "right" or a "left" configuration to be implanted on the right or left lateral side of the vertebrae. However, only one (right or left) configuration will be described, and it is assumed that the other (right or left) configuration is a mirror-image of the one described. It is also appreciated that the implants described herein may be implanted bi-laterally as in FIG. 1, or unilaterally, if desired.

Figure 2:
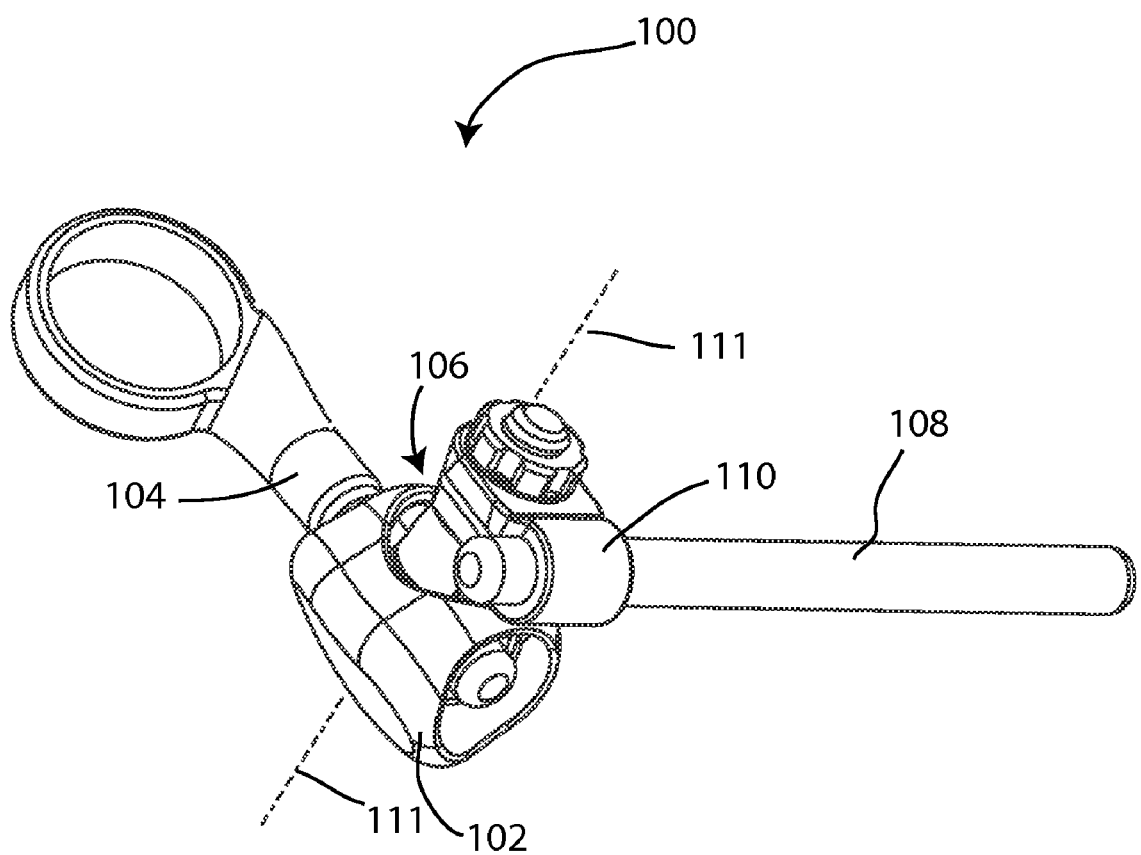
FIG. 2 is perspective view of an inferior facet joint implant coupled to a crosslink rod.

Referring to FIG. 2, a perspective view depicts polyaxially adjustable left inferior facet joint implant 100. Inferior facet joint implant 100 comprises an inferior articular body 102, an inferior strut 104, and an attachment mechanism 106 which adjustably secures the articular body to the inferior strut. The attachment mechanism 106 has an adjustable configuration in which the inferior articular body 102 can rotate relative to the inferior strut 104 about three orthogonal axes, and it has a locked configuration in which the inferior articular body 102 is rigidly secured to inferior strut 104. A crosslink rod 108 may optionally be secured to the implant 100 by a split clamp 110. The attachment mechanism 106 may be actuated to simultaneously lock the crosslink rod 108 in the split clamp 110 as the inferior articular body 102 is locked to the inferior strut 104. A clamp axis 111 extends longitudinally through the attachment mechanism.

Figure 3:
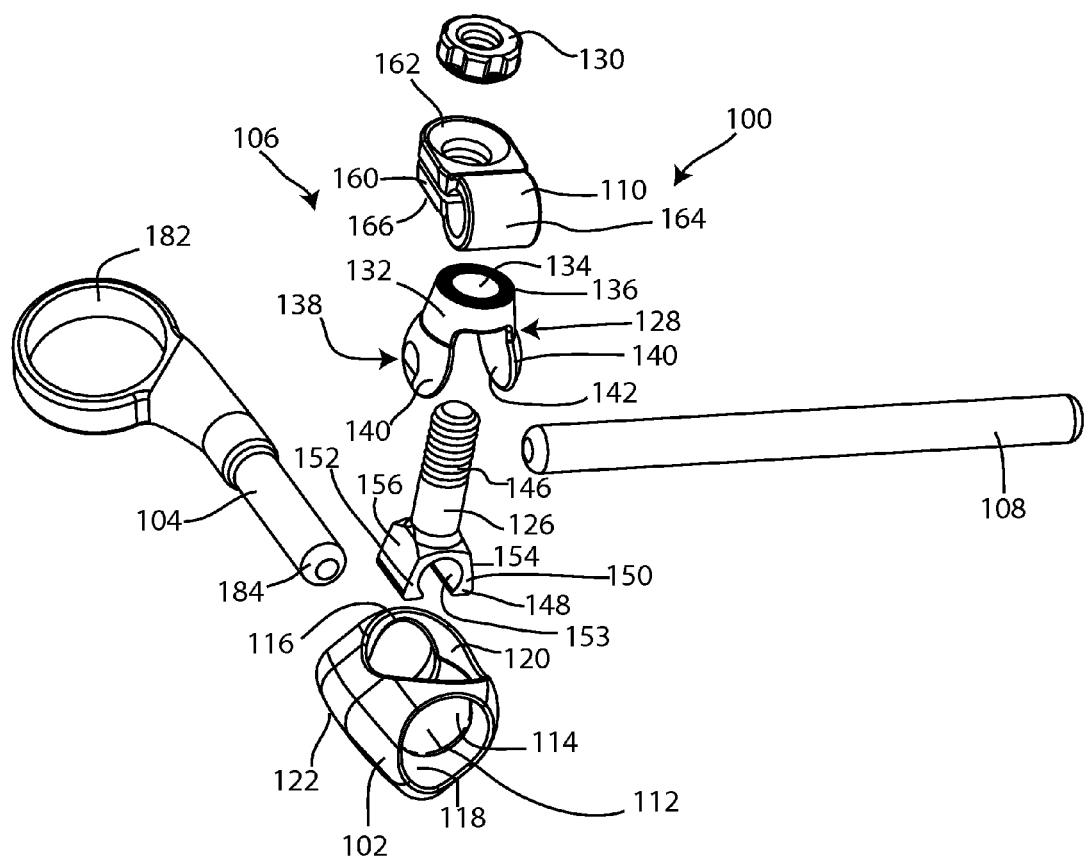
FIG. 3 is an exploded view of the inferior facet joint implant and crosslink rod of FIG. 2.

Referring to FIG. 3, an exploded perspective view illustrates the component parts which may comprise the left inferior facet joint implant 100. The inferior articular body 102 is shell-like and has a substantially concave interior cavity 112 which is defined by an interior wall 114. A first chamfered opening 116 and a second chamfered opening 118 in the inferior articular body 102 create a passageway through which a portion of the inferior strut may fit when the implant is assembled. An attachment post opening 120, which may also be chamfered, is situated orthogonal to the first and second chamfered openings 116, 118. The chamfered openings may provide additional range of motion between the inferior articular body and the inferior strut 104 as the articular body 102 is polyaxially adjusted prior to locking down. An inferior articular surface 122 is located on the exterior of the inferior articular body 102, and is shaped to replace a natural inferior articular surface of a vertebra. Inferior facet implant 100 may be implanted in conjunction with a superior facet implant, wherein the inferior articular surface 122 articulates with an artificial superior facet articular surface. Alternately, inferior facet implant 100 may be implanted such that the inferior articular surface 122 articulates with a natural superior facet articular surface.

Figure 4:
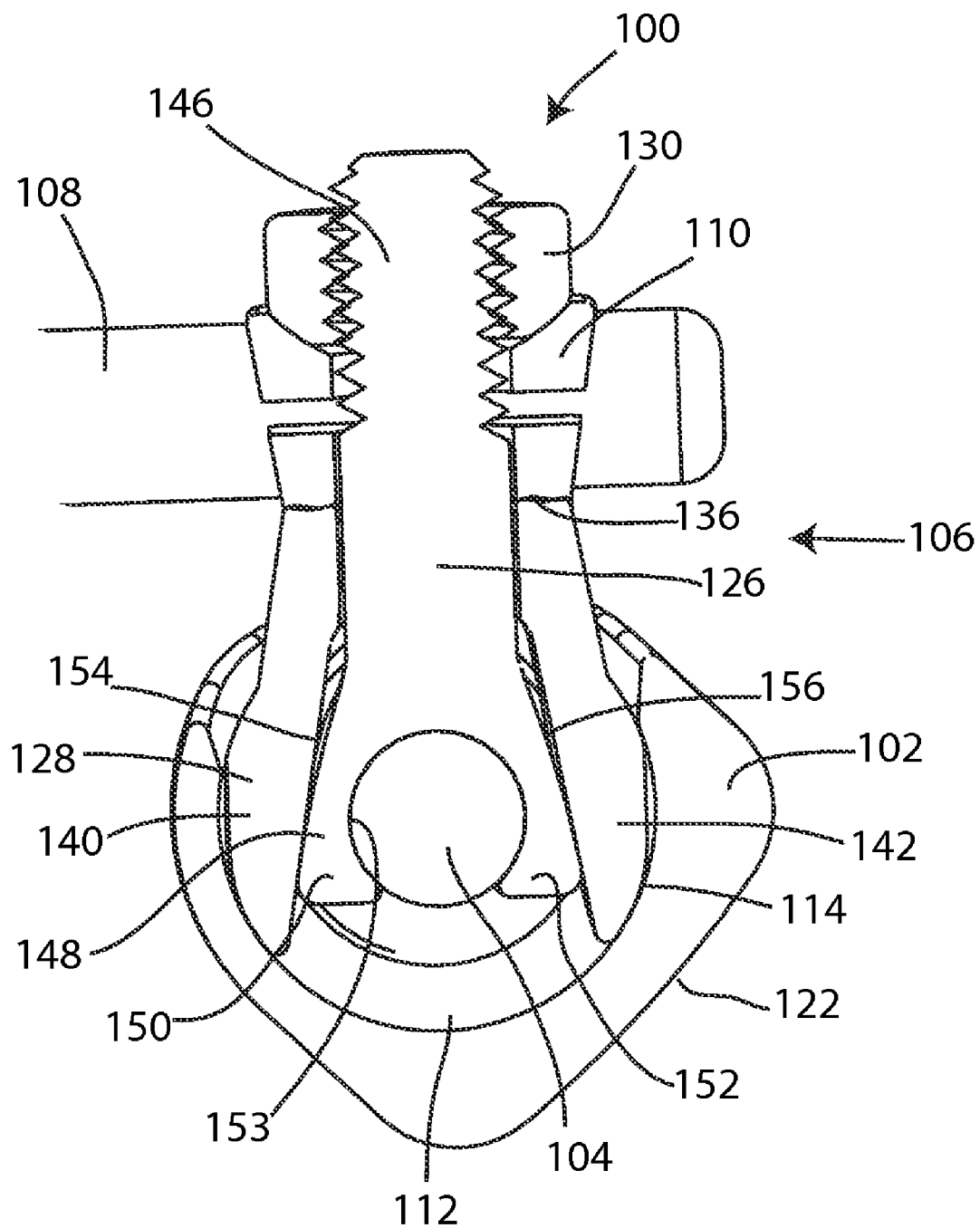
FIG. 4 is a partial cross-sectional view of an attachment mechanism of the facet joint implant of FIG. 2.

FIG. 4 displays the attachment mechanism in a cross-sectional view. The attachment mechanism 106 is configured to provide polyaxial adjustability between the inferior articular surface 122 and the inferior strut 104. Once the desired orientation of the articular surface 122 relative to the inferior strut 104 is reached, the attachment mechanism 106 may be locked down, securing the articular surface to the inferior strut. Referring to FIGS. 3 and 4, the attachment mechanism comprises a locking member which is a threaded conical expander 126, an expandable member which is a split shell 128, the split clamp 110, and a nut 130.

The split shell 128 has a circular neck portion 132 through which passes a bore 134. The bore opening is surrounded by a radial spline 136. Adjacent to the neck portion 132 is a spherical portion 138 which comprises two expandable lobes 140, 142. An interior surface 143 of the lobes 140 may be tapered. The present embodiment of the invention includes two lobes, however it is appreciated that more lobes may be included, or other expandable portions, in other embodiments. The split shell 128 fits over the conical expander 126 such that a threaded post 146 of the conical expander passes through the bore 134. An expansion portion 148 of the conical expander 126 is forked and has two opposing flanges 150, 152 which are shaped to fit around and grip the inferior strut 104. An inner wall 153 of the flanges is curved to fit around the inferior strut, and the outer walls 154, 156 are tapered.

The split ring clamp 110 comprises an inner ring 160, an outer ring 162 and a collar 164 which joins the inner and outer rings. The collar 164 is shaped to fit around and grip the crosslink rod 108. The split ring clamp is configured such that when the inner and outer rings 160, 162 are compressed together, a diameter of the collar 164 decreases and the collar can tighten around and secure the crosslink rod. The surface of an exterior side of the inner ring 160 is a radial spline 166, which is shaped to engage with the radial spline 136 on the split shell 128.

When assembled, the split shell 128 fits over the conical expander 126, and the two parts fit within the inferior articular body 102 such that the interior cavity 112 houses the expansion portion 148 of the conical expander 126 nested inside the spherical portion 138 of the split shell 128. The conical expander 126, split shell 128 and inferior articular body 102 are oriented so that in general the flanges 150, 152 are adjacent to the lobes 140, 142, and the lobes are adjacent to the interior wall 114 of the interior cavity 112. A rod portion of the inferior strut 104 fits between the flanges 150, 152 of the conical expander.

The split ring clamp 110 fits over the threaded post 146 of the conical expander so that the radial spline 166 of the split clamp meets the radial spline 136 of the split shell 128. The crosslink rod 108 extends through the collar 164 of the split clamp. The nut 130 is threaded onto the threaded post 146 of the conical expander.

Until the attachment mechanism 106 is locked down by actuating the nut 130, the implant is adjustable in multiple ways. The crosslink rod 108 has relative angular freedom of motion about the clamp axis 111 and the inferior strut axis. The position of the crosslink rod 108 relative to the split clamp 110 may be adjusted such that a relatively longer or shorter length of the crosslink rod 108 extends through the clamp. This provides an opportunity to select the best fit to the patient's anatomy and the specific vertebral level being treated. Similarly, the position of the inferior strut 104 may be adjusted relative to the inferior articular body 102 such that a relatively longer or shorter length of the inferior strut 104 extends through the flanges 150, 152 of the conical expander 126. Also, the inferior strut 104 has relative angular freedom of motion about the clamp axis 111. The inferior articular body 102 may be polyaxially rotated about the conical expander 126 and the split shell 128. The adjustments provide relative rotation between the inferior articulation surface 122 and the inferior strut 104 about three orthogonal axes. In addition, prior to lockdown, relative translation between the inferior strut 104, the inferior articulation surface 122, and the crosslink 108 is permitted.

The attachment mechanism 106 is locked down by actuating, or turning the nut 130. As the nut is turned and its threads engage the threaded post 146, the conical expander 126 is urged "upward" through the nut 130, while the outer ring 162 of the split clamp 110 is urged "downward" toward the inner ring 160. As the conical expander 126 moves, the flanges 150, 152 push against the lobes 140, 142 of the split shell 128, and in turn the lobes expand and push against the interior wall 114 of the interior cavity 112. Simultaneously, the flanges 150, 152 are compressed around the inferior strut 104. Similarly, the collar 164 of the split clamp 110 is compressed around the crosslink rod 108 as the inner 160 and outer 162 rings of the clamp are urged together. The nut 130 may be actuated until the resulting internal compression prevents any further motion, and the mechanism is locked down.

The inferior implant 100 may be delivered in an assembled, but not locked down, configuration. The crosslink rod 108 may be included in the assembly, provided separately, or excluded. The inferior implant 100 may be delivered in combination with a superior implant, in which a clip or other temporary fastener holds the inferior articular surface to a superior articular surface of the superior implant.

Figure 5:
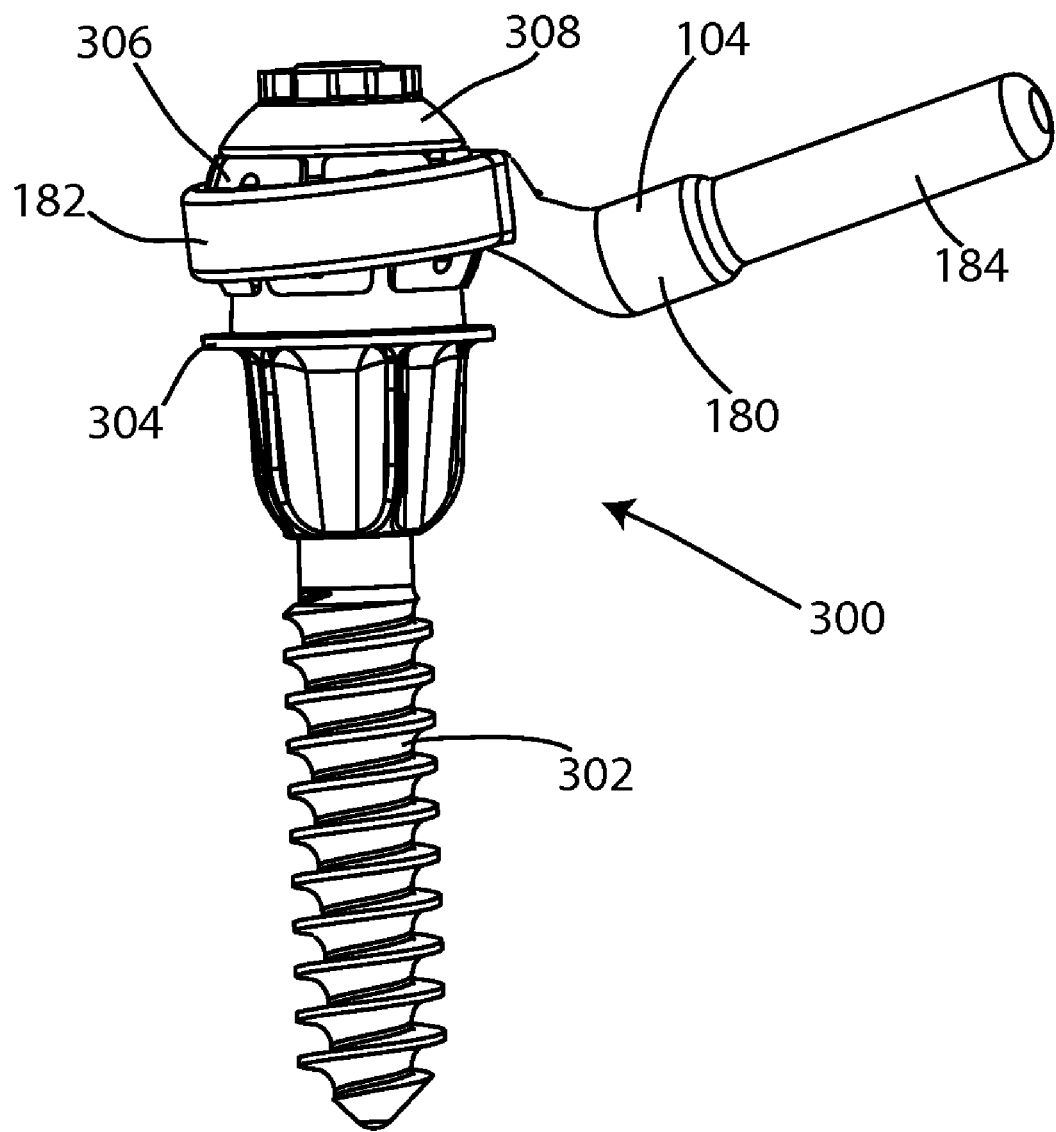
FIG. 5 is a perspective view of a fixation assembly secured to an inferior strut.

Referring to FIG. 5, inferior strut 104 is shown coupled to fixation assembly 300, which may also be termed an attachment mechanism. Fixation assembly 300 is configured to be implanted in a pedicle of a vertebra, and to be coupled to inferior implant 100 or another implant. The fixation assembly 300 is polyaxially adjustable, and comprises a fixation member 302, a tapered base 304, a split sphere 306, and a top nut 308. The inferior strut 104 is generally elongated in configuration, with a central portion 180, a first end which is a ring 182, and a second end which is a strut post 184. The ring 180 may be set at an angle relative to the central portion 180 and the strut post 184. Conversely, the strut post 184 may be at an angle relative to the central portion and the ring; also the central portion 180 may be straight, bent or curved.

Figure 6:
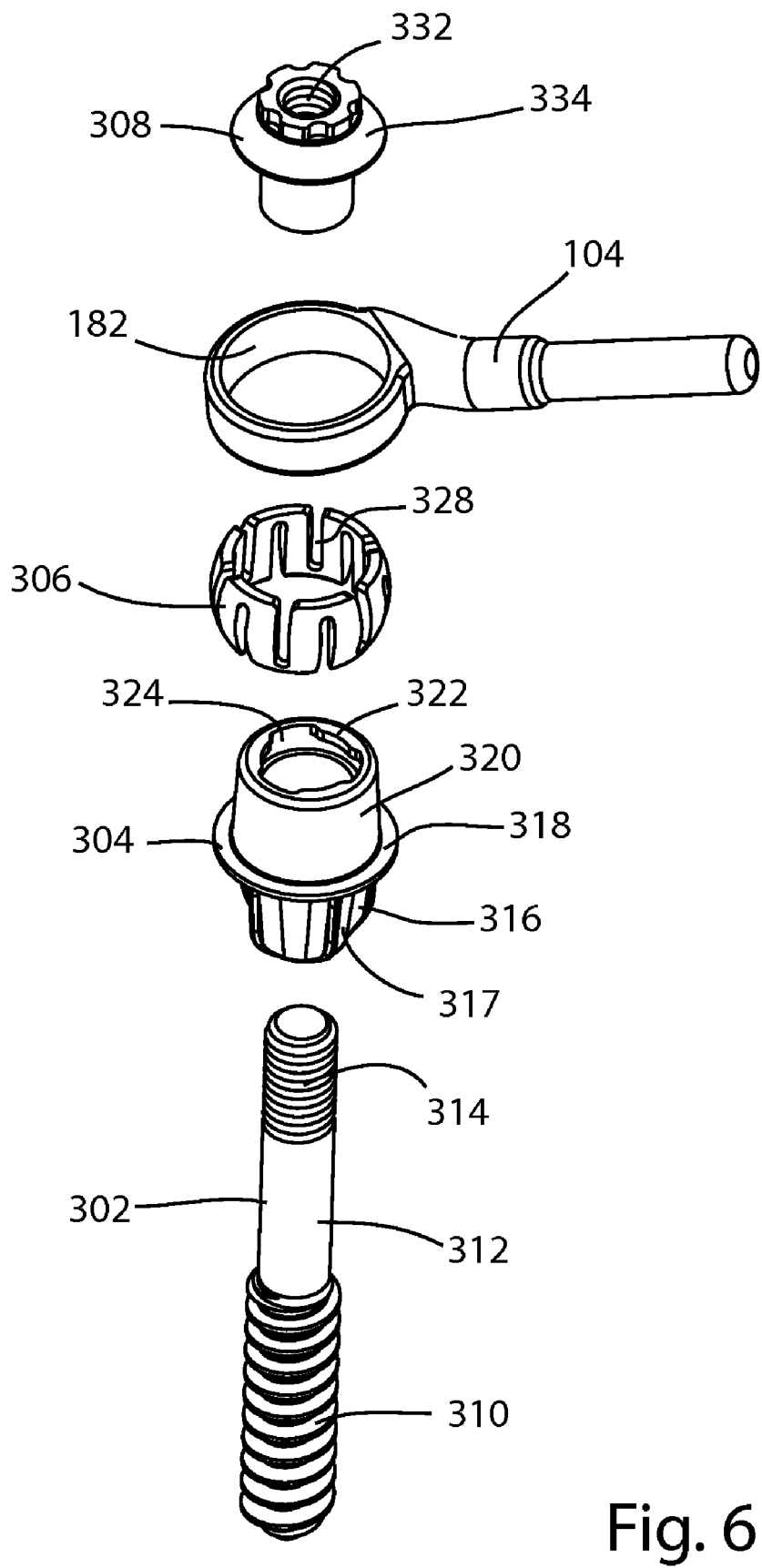
FIG. 6 is an exploded view of the fixation assembly and inferior strut of FIG. 5.

FIG. 6 is an exploded view of the inferior strut 104 and the fixation assembly 300. The fixation member 302, which may be a pedicle screw, has a threaded fixation portion 310, a shaft 312, and a threaded attachment portion 314. The tapered base 304 is cannulated throughout, and has an inset portion 316, a flange 318 and a tapered portion 320. The inset portion may be tapered to provide compression to the surrounding bone, and may have a plurality of fins 317 which prevent rotation of the base 304 in the bone. In alternate embodiments of the invention, the inset portion 316 may include teeth, studs, fins, or combinations thereof, or other anti-rotation features, or no anti-rotation features. At an open end of the tapered portion 320, a tool engagement rim 322 includes a plurality of notches 324. The split sphere 306 is sized to fit over the tapered portion 320 of the base 304, and includes a plurality of slits 328 which allow the sphere to be expandable. The top nut 308 has a threaded bore 332 and a flange 334 which encircles the nut 308.

The fixation assembly 300 may be delivered in a partially assembled state or be assembled from the components described above. During implantation, the fixation member 302 may be implanted in the pedicle of the vertebra using methods known in the art. The tapered base 304 is fit over the shaft of the fixation member 302. The split sphere 306 fits over the tapered portion 320 of the base 304. The ring 182 of the inferior strut 104 is placed so it encircles the split sphere 306. At this point, the ring 182 may be polyaxially adjusted around the split sphere so that the inferior strut 104 attains a desired orientation. To lock down the desired orientation, a compression lockout tool (not shown) engages the notches 324 of the tool engagement rim 322 on the base 304. The lockout tool provides compression on the split sphere 306, urging it farther onto the tapered portion 320 toward the flange 318. As the split sphere 306 moves down the tapered portion 320, it expands and engages the ring 182 of the inferior strut 104. Once all motion between the tapered portion 320, split sphere 306 and ring 182 is locked out, the tool is removed. The top nut is threaded onto the threaded attachment portion 314 of the fixation member 302, to retain the base 302, sphere 306 and ring 182 on the fixation member, and to further secure the inset portion 316 in the vertebra. Optionally, the base 304, split sphere 306, and ring 182 may be assembled and locked out independently of the fixation member 302, then dropped onto the fixation member 302 and retained with the top nut 308. The inferior implant 100 may be secured to the inferior strut 104 before or after the inferior strut 104 is locked into position with the base 304 and split sphere 306.

Figure 7:
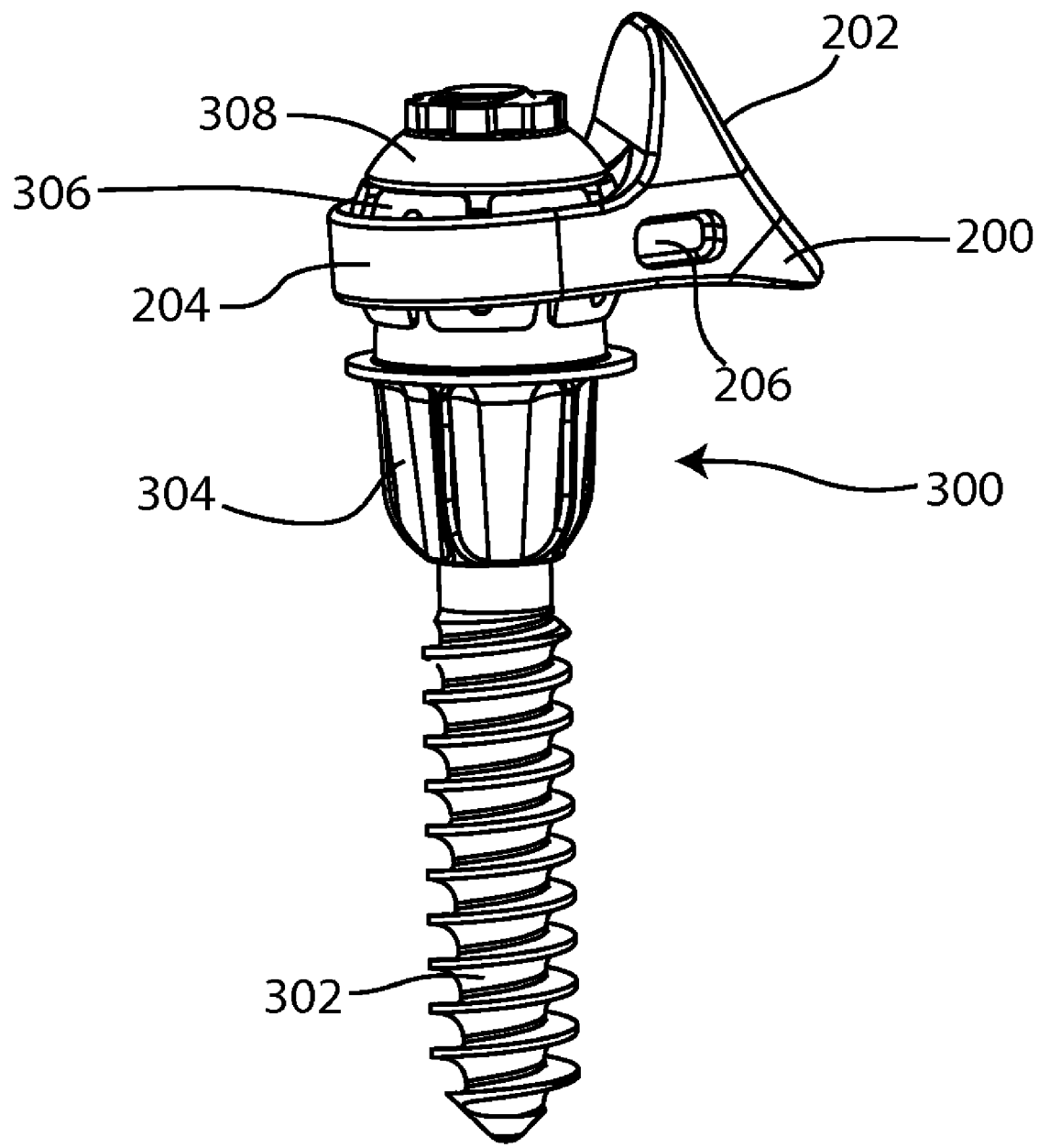
FIG. 7 is a perspective view of a fixation assembly secured to a superior facet joint implant.

Referring to FIG. 7, the superior implant 200 is shown secured to the fixation assembly 300. The superior implant 200 may be monolithic and includes a superior articulation surface 202 shaped to replace a natural superior articular surface of a vertebra, a ring 204, and may include at least one notch-like gripping feature 206. The superior implant 200 may be secured to the fixation assembly 300 in the same method as described previously for the inferior strut 104. The ring 204 of the superior implant 200 is locked in position relative to the split sphere 306 and the base 304. The base 304, split sphere 306 and implant 200 may be dropped over an implanted fixation member 302, and the top nut 308 secured on the fixation member to retain the assembly. The superior implant 200 may be delivered in combination with an inferior implant 100, and the superior articular surface 202 may be temporarily clipped to the inferior articular surface 122.

Returning to FIG. 1, the components comprising the fixation assembly 300, superior 200, 201 and inferior 100, 101 implants and crosslink 108 may be implanted as follows. The pedicles are prepared for implantation, which may include removal of natural facet surfaces and bone preparation, and may include a broaching step to shape the pedicles to receive the base components. Broaching may ensure bone ingrowth and better mechanical retention of the bases and therefore the full implant system. Initially the fixation member 302 for each fixation assembly 300 is driven into the pedicles to a prescribed or desired depth. A tapered base 304 is placed on each fixation assembly 300. A split sphere 306 is placed on the bases intended for the superior implants, and the superior implants 200, 201 are placed over the split spheres, and locked down relative to the fixation assembly as described previously. Alternatively, the split sphere 306 may be captured in the ring 204 of the implant 200 or 201, and the implant/ring assembly placed in the base 304.

Next, the inferior implants 100, 101 are each assembled with an inferior strut 104, but not yet locked to the strut. A split sphere 306 is captured in the ring 182 of each strut 104, and each inferior implant/strut/sphere assembly is placed on a base intended for an inferior implant. At this point, the inferior articular surfaces are aligned with the superior articular surfaces, and may be temporarily clipped together to maintain the alignment. The inferior implant/strut assemblies are locked down to the fixation assemblies.

The crosslink 108 may now be inserted through the collar 164 of the split clamp 110 of one inferior implant 100 or 101 and optionally through a prepared spinous process, and through the other collar 164 on the remaining inferior implant 100 or 101. It is appreciated that as the crosslink 108 is inserted, the split clamp 110 is rotatable about the clamp axis 111. Therefore, the crosslink 108 may be positioned to pass through a spinous process, or may pass through soft tissue caudal to the spinous process. Alternatively, the crosslink 108 may be inserted before the inferior implants are locked down to the fixation assemblies. The attachment assemblies 106 of each inferior implant 100, 101 are actuated to lock down the implants, fixing the positions of the articular surfaces 122, the inferior struts 104 and the crosslink 108.

Some variation in the steps described above may occur. For example, the inferior articular body 102 may be available packaged with the superior implant 200, temporarily clipped together such that the articular surfaces 122, 202 are in a desired alignment. In this instance, the inferior articular body 102 is inserted with the superior implant 200 as the superior implant 200 is placed and locked with the fixation assembly 300. Then the inferior strut 104 and the remaining components of the inferior implant 100, including the conical expander, split shell, and split clamp are assembled with the inferior articular body 102. The ring 182 of the inferior strut 104 is assembled and locked down with the inferior fixation assembly 300. The insertion of the crosslink 108 and final lockdown is as described previously, and the clip is removed.

Alternatively, the inferior implant 100 may be available secured to a clip. The implant 100, with the attached clip, may be inserted adjacent to an already implanted and locked down superior implant, and the inferior and superior implants temporarily clipped together. The inferior strut is adjusted and locked down to its fixation assembly. The insertion of the crosslink 108 and final lockdown of the inferior implant is as described previously, and the clip is removed.

System 10, and other facet replacement components disclosed herein, may also be implanted on multiple vertebral levels to provide facet joint replacement across several levels. In a multi-level application, additional superior implants could be added to the fixation members 300 which secure the inferior struts 104, to extend the system in a cephalad direction. Similarly, to extend the system caudally, additional inferior struts coupled to inferior implants could be added to the fixation members 300 which secure the original superior implants 200. Also, fusion rods (not shown) may be secured between fixation members 300 on adjacent vertebra to provide rigid fusion at a desired vertebral level.

Figure 8:
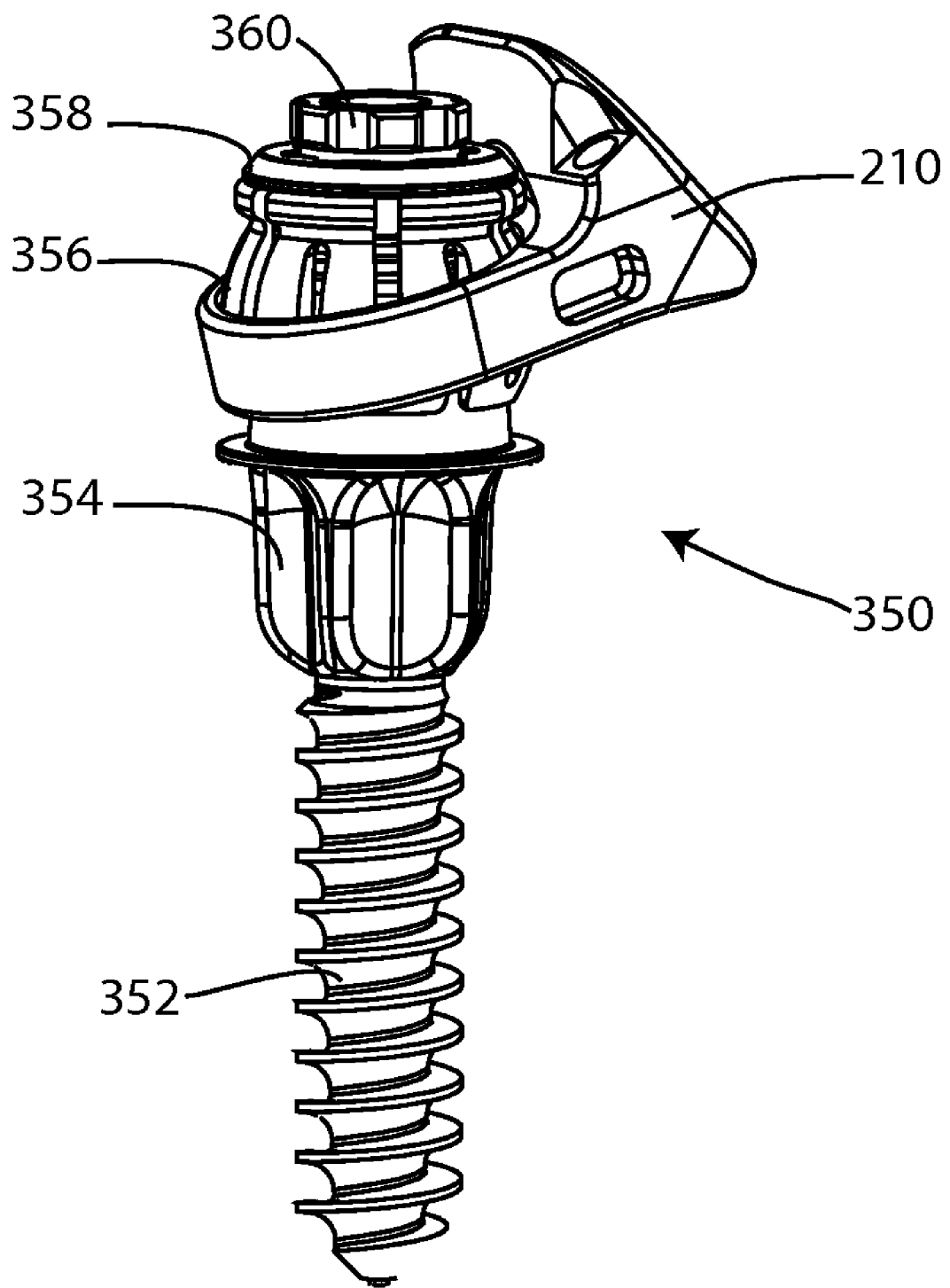
FIG. 8 is a perspective view of an alternate fixation assembly secured to a superior facet joint implant.
Figure 9:
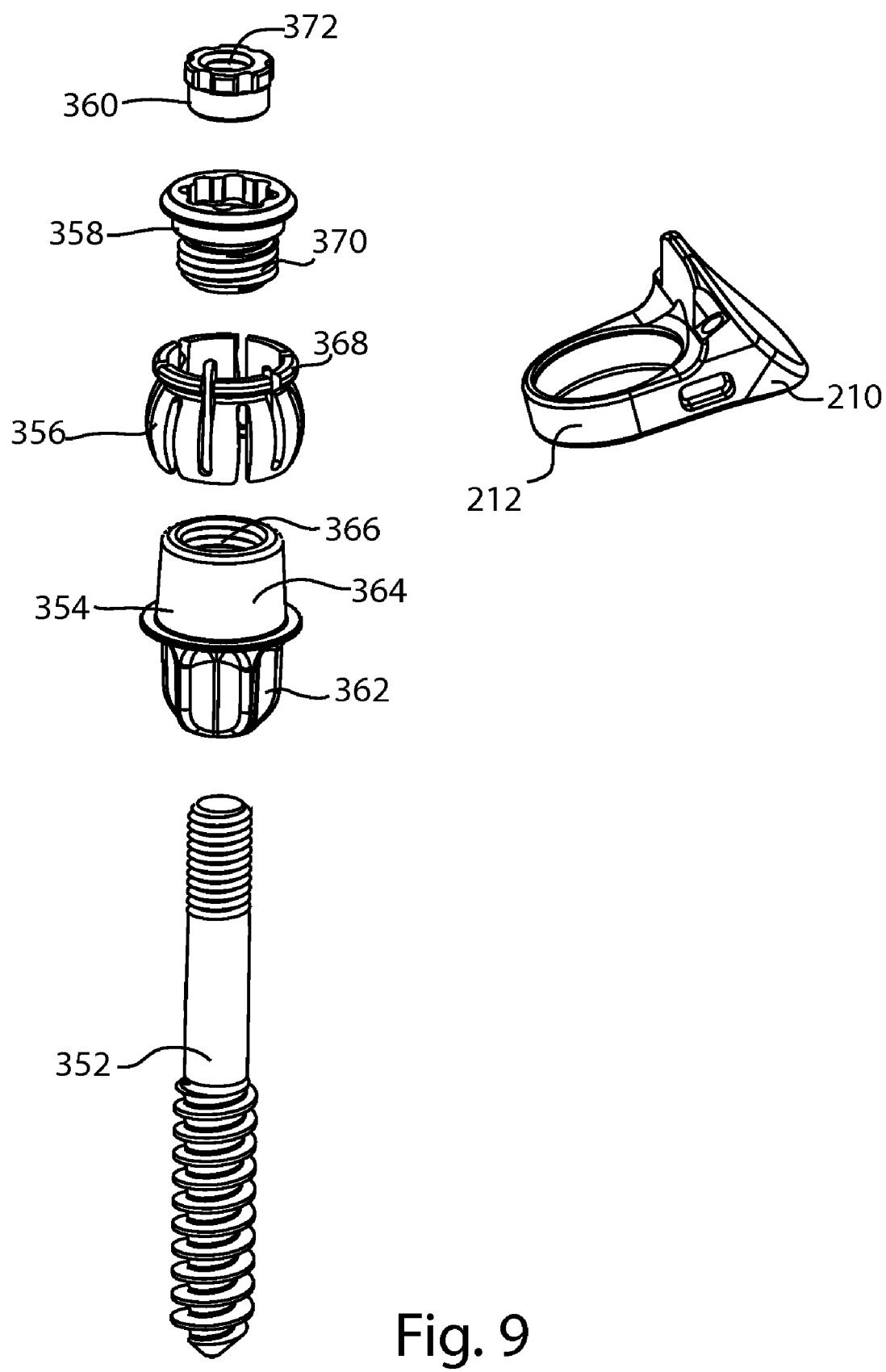
FIG. 9 is an exploded view of the alternate fixation assembly and superior facet joint implant of FIG. 8.
Figure 10:
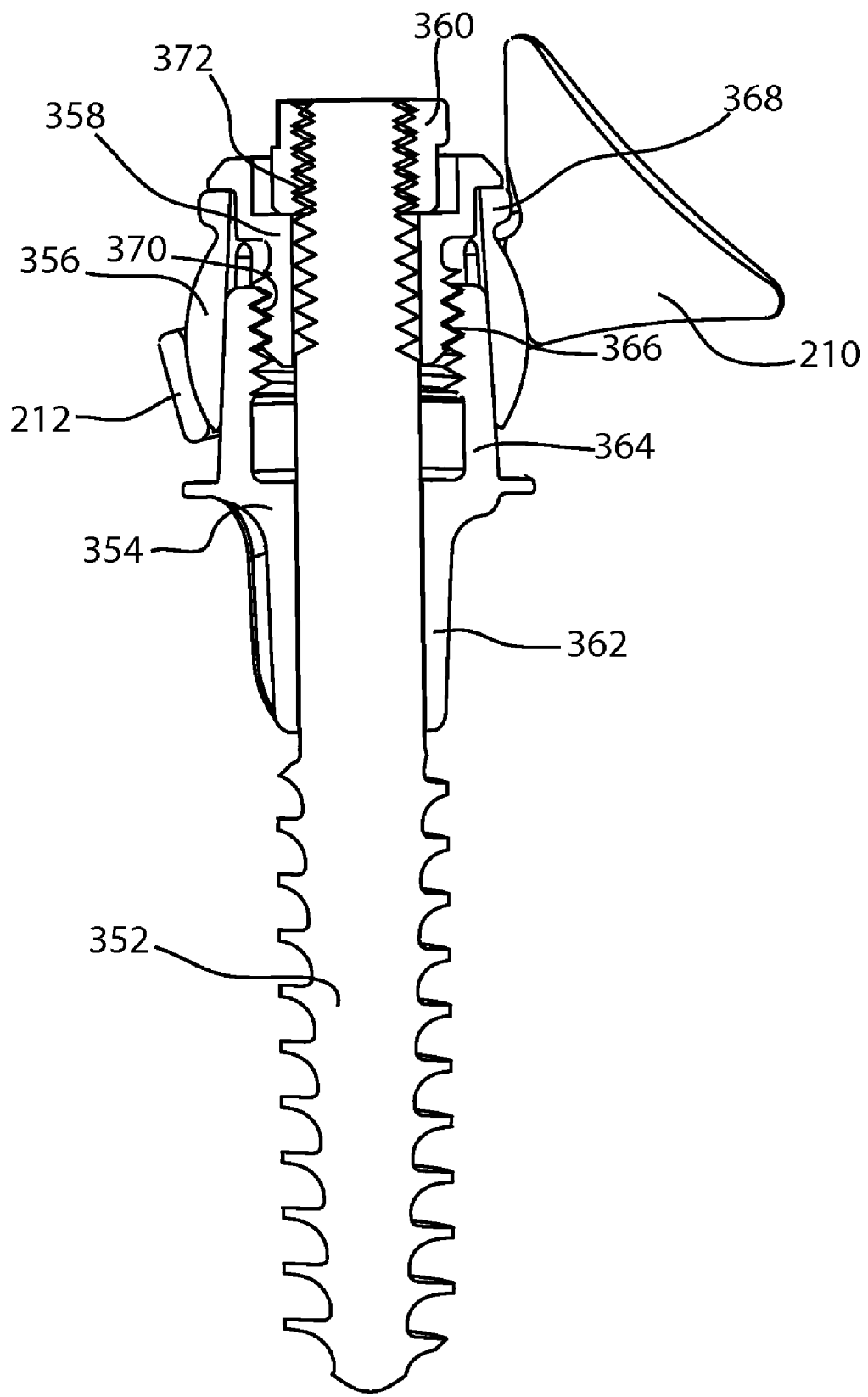
FIG. 10 is a partial cross-sectional view of the alternate fixation assembly and superior facet joint implant of FIG. 8.

FIG. 8 presents an alternative embodiment of a polyaxially adjustable fixation assembly 350 with an alternative embodiment of a superior implant 210. FIG. 9 presents an exploded view of fixation assembly 350, and FIG. 10 presents a cross-sectional post-assembly view of the assembly. With reference to all three figures, fixation assembly 350 comprises a fixation member 352, a tapered base 354, a flanged split sphere 356, a capture nut 358, and a top nut 360. The cannulated tapered base 354 has an insert portion 362 which may include anti-rotation features such as fins, teeth or studs. A tapered portion 364 has a threaded lumen 366. The split sphere 356 includes a split flange 368 which encircles one open end of the sphere. The capture nut 358 has a threaded outer surface 370, while the top nut 360 has a threaded inner surface 372. Fixation assembly 350 may also be termed an attachment mechanism. It is appreciated that fixation assembly 350 may be substituted for fixation member 300 in any fixation procedure disclosed or depicted herein, and vice versa. Also, a combination of fixation assemblies 300 and 350 may be used.

The fixation member 352 is initially implanted into the pedicle, and the tapered base 354 is inserted over the fixation member 352 and seated in the bone. The split sphere is placed over the tapered portion 364 of the tapered base 354. A ring 212 of the superior implant 210 is placed around the split sphere 356. At this point, the ring 212 may be polyaxially adjusted to attain a desired orientation of the superior implant 210. To lock the orientation and position of the superior implant 200, a lockout tool (not shown) is actuated to effect the taper lock. The lockout tool has an externally threaded inner shaft tip which is engaged in the threaded lumen 366 of the tapered base 354. The lockout tool is actuated, using tensile force to simultaneously pull on the tapered base 354 with the inner shaft, and push on the flange 368 of the split sphere 356 with an outer shaft. This force moves the split sphere 356 farther onto the tapered portion 364. The split sphere 356 expands and engages the ring 212 of the superior implant 210 until all motion ceases and the position of the ring 212 is locked down. The lockout tool is unthreaded and removed, and the capture nut 358 is threaded into the tapered lumen 366, also capturing the flange 368 of the split sphere 356. The capture nut 358 is included to ensure the long-term integrity of the lock. The top nut 360 is threaded onto the fixation member 352, and assists in holding the tapered base 362 against the bone surface. The top nut 360 and capture nut 358 may use the same driver.

Figure 11:
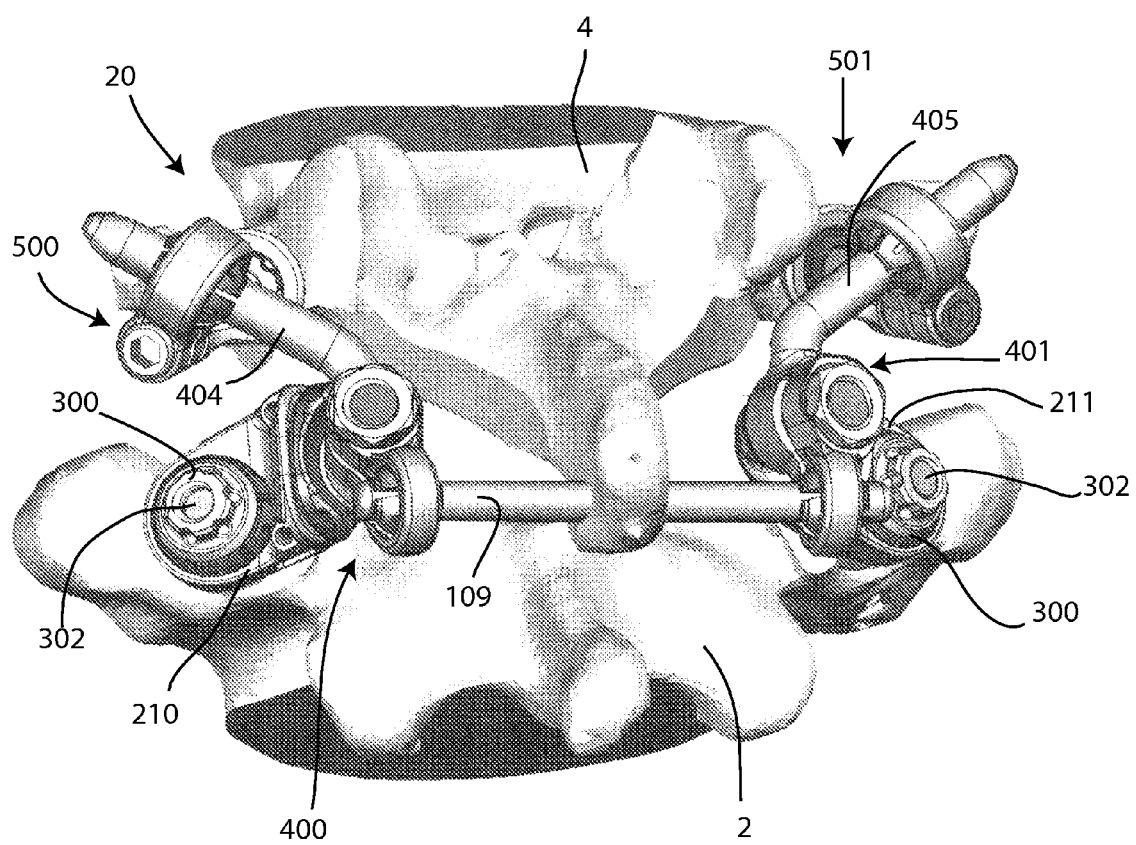
FIG. 11 is a perspective view of a portion of a spine with an alternate bi-lateral facet joint replacement system implanted into two adjacent vertebrae.

Referring to FIG. 11, a perspective posterior view depicts an alternative embodiment of a bi-lateral facet joint replacement system 20, implanted in two vertebrae. On the left lateral side, a superior implant 210 is secured to the first vertebra 2 by a fixation assembly 300. The superior articular surface articulates with an inferior articular surface of an inferior implant 400. An adjustable attachment mechanism couples an inferior implant body to one end of an inferior strut 404, and a crosslink rod 109 which crosses a sagittal plane of the vertebrae. An opposite end of the inferior strut is secured to the second vertebra 4 by a fixation assembly 500. On the right lateral side, a mirror-image of the system is implanted, including superior implant 211, second fixation assembly 300, inferior implant 401, inferior strut 405 and fixation assembly 501. The crosslink rod 109 links the left inferior implant 400 to the right inferior implant 401. As previously set forth, only one lateral side of the system will be depicted and described.

Figure 12:
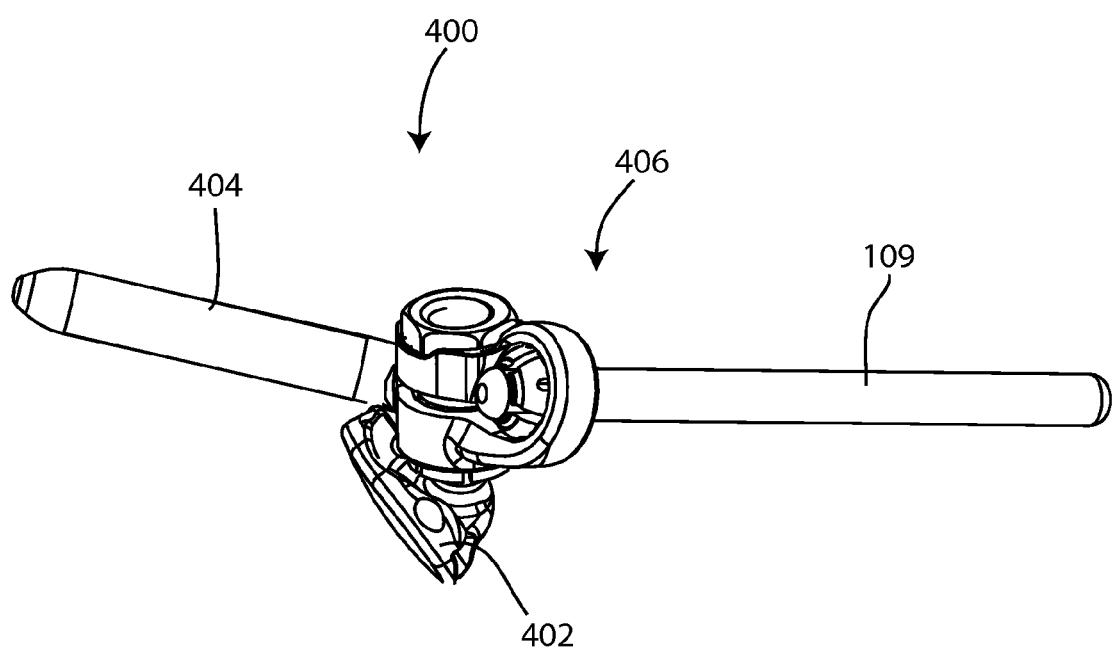
FIG. 12 is a perspective view of an inferior facet joint implant coupled to a crosslink rod.

FIG. 12 depicts the inferior implant 400, which comprises an inferior articular body 402, an inferior strut 404, and an attachment mechanism 406 which adjustably secures the articular body to the inferior strut. The crosslink rod 109 may be also secured to the inferior implant 400 by the attachment mechanism 406. Attachment mechanism 406 may have two configurations: an adjustable configuration in which there is relative rotation between the inferior articular body 402, the inferior strut 404 and the crosslink rod 109, and a locked configuration in which the inferior articular body 402, the inferior strut 404 and the crosslink rod 109 are rigidly secured to each other.

Figure 13:
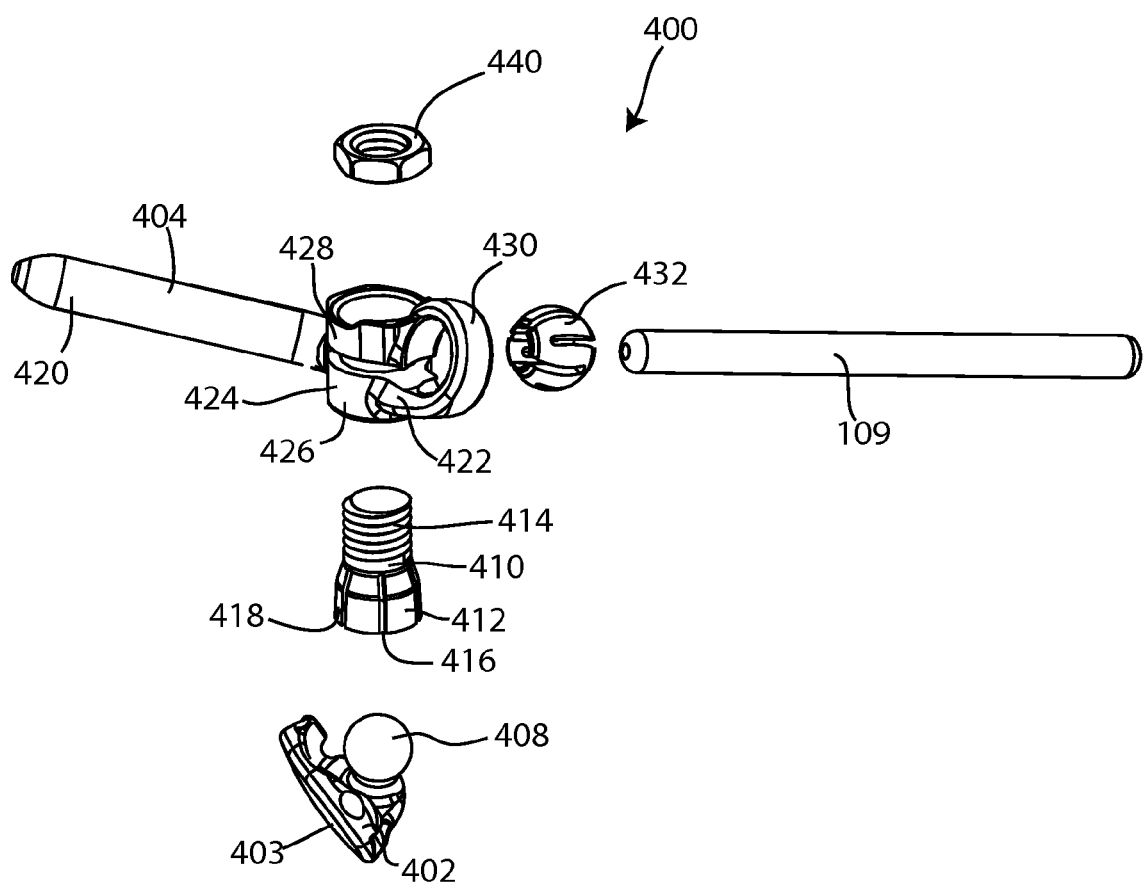
FIG. 13 is an exploded view of the inferior facet joint implant and crosslink rod of FIG. 12.

FIG. 13 is an exploded view of the inferior articular body 402, inferior strut 404, crosslink rod 109 and the attachment mechanism 406. The inferior articular body 402 is monolithic and comprises an inferior articulation surface 403 shaped to replace a natural inferior articular surface of a vertebra, and a connection feature which has a rounded surface 408, which in this embodiment is a spherical surface. A compressible member 410 includes a conical portion 412 and a threaded post 414. The conical portion 412 has an interior cavity 416 encircled by a plurality of expandable fingers 418. The interior cavity 416 is shaped to receive the rounded surface 408.

The inferior strut 404 has a first end 420 which is shaped as a rod, and a second end 422 which is shaped as a ring. The second end 422 comprises a split ring clamp 424, the split ring having an inner ring 426, an outer ring 428, and a collar 430, which connects the inner and outer rings. The collar 430 is oriented generally orthogonal to the inner and outer rings. The collar 430 is shaped to receive a split sphere 432, which has an interior shaped to receive the crosslink rod 109. A nut 440 is configured to be threaded on the threaded post 414.

Figure 14:
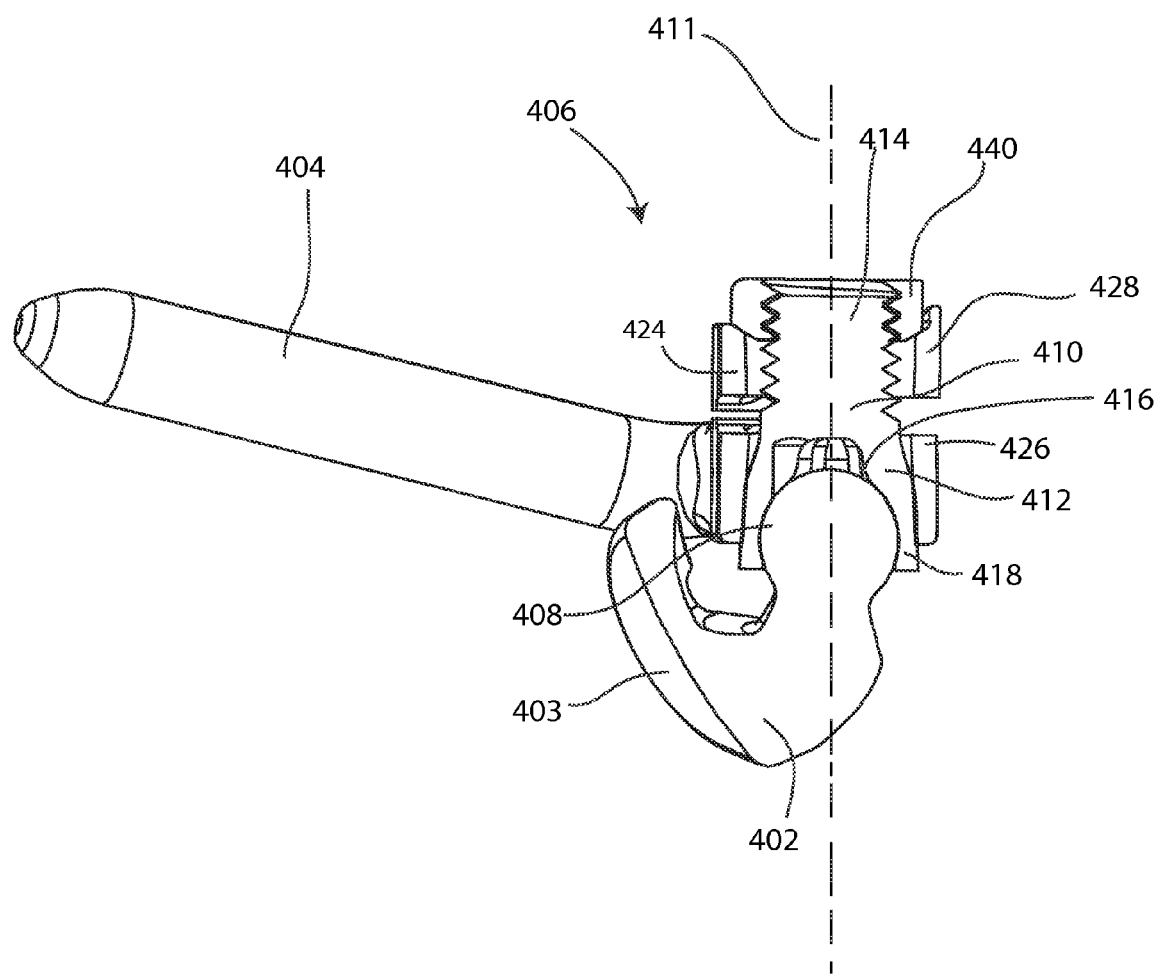
FIG. 14 is a partial cross-sectional view of the inferior facet joint implant of FIG. 12.

FIG. 14 is a partial cross-sectional view of the attachment mechanism 406 components in the locked configuration (the collar 430, split sphere 432 and crosslink 109 are not visible in this figure). A clamp axis 411 extends longitudinally through the attachment mechanism. As described previously, the rounded surface 408 is received in the cavity 416 of the compressible member 410. The split ring clamp 424 fits around the compressible member 410, with the inner ring 426 around the conical portion 412 and the outer ring 428 around the threaded post 414. The collar 432 fits around the split sphere 432, which receives the crosslink rod 109. Also with reference to FIG. 13, when thus assembled but not locked down, the attachment mechanism 406 is adjustable in multiple ways. The inferior articular surface 403 may be polyaxially rotated relative to the inferior strut 404 and the crosslink rod 409. The split sphere encompassing the crosslink rod 109 may be polyaxially rotated within the split ring clamp 424 relative to the inferior strut 404 and the inferior articular surface 403. A length of the crosslink rod 109 which extends through the attachment mechanism 406 may be adjusted. The inferior strut 404 has relative angular freedom of motion about a clamp axis 411. These adjustments provide relative rotation between the inferior articulation surface 403 and the inferior strut 404 about three orthogonal axes. In addition, prior to lockdown, relative translation between the inferior strut 404, the inferior articulation surface 403, and the crosslink 109 is permitted. An attachment mechanism 407, for the right side of the vertebrae, is configured as a mirror image of attachment mechanism 406.

The attachment mechanism 406 is locked down by actuating, or turning the nut 440. Lockdown of the attachment mechanism locks out both the position of the inferior strut relative to the inferior articulation surface, and the position of the crosslink. As the nut is turned and its threads engage the threaded post 414, the compressible member 410 is urged "upward" through the nut 440, while the outer ring 428 of the split ring clamp 424 is urged "downward" toward the inner ring 426. As the compressible member 410 moves, the tapered outer wall of the conical portion 412 engages the inner surface of the inner ring 426. Simultaneously, the interior wall of the conical portion 412 exerts compressive force against the rounded surface 408 in the interior cavity 416. Similarly, the collar 430 of the split ring clamp 424 is compressed around the split sphere 432, which compresses around the crosslink rod 109, as the inner 426 and outer 428 rings of the clamp are urged together. The nut 440 may be actuated until the resulting internal compression prevents any further motion, and the mechanism is locked down.

Figure 15:
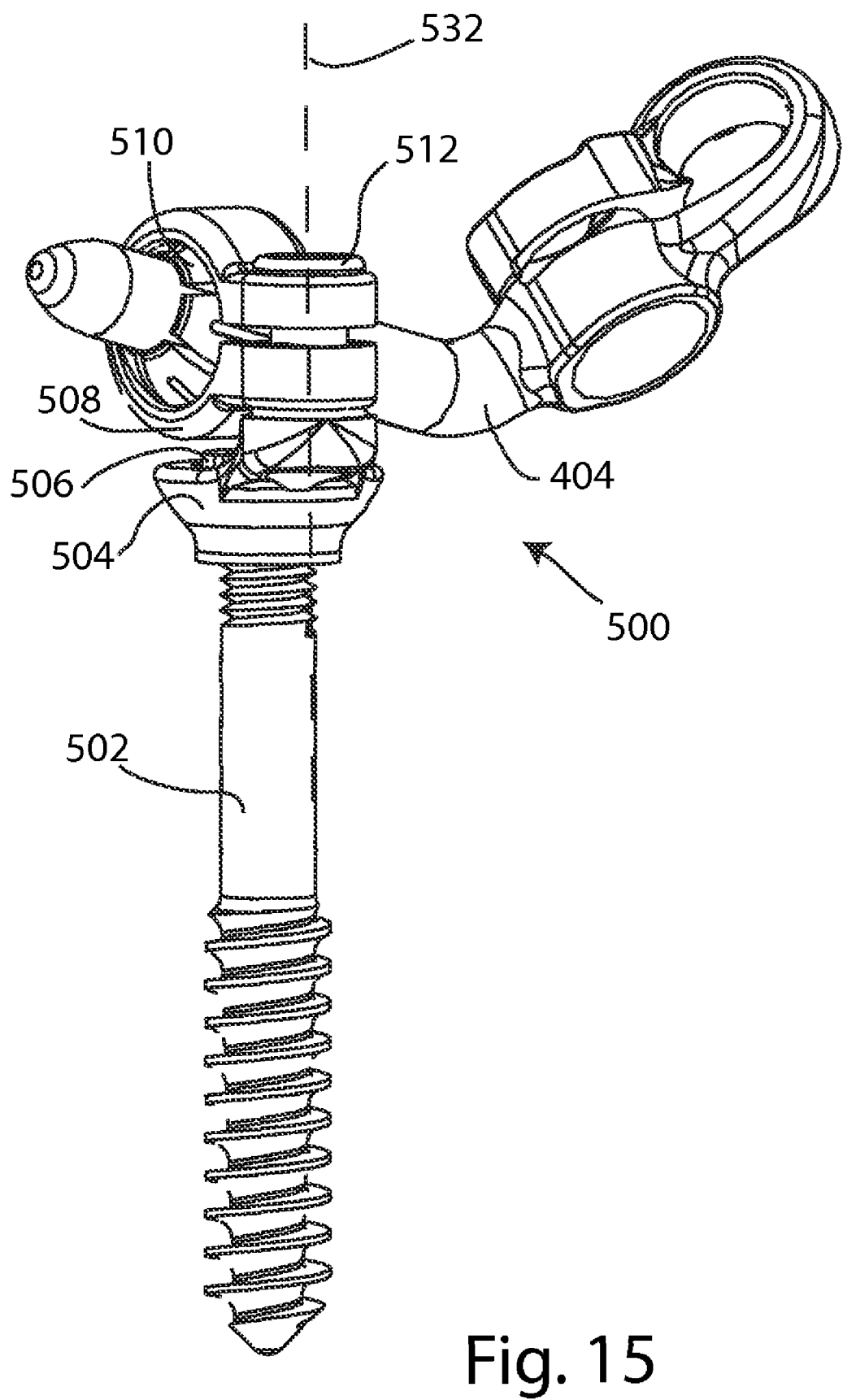
FIG. 15 is a perspective view of a fixation assembly and an inferior strut.

FIG. 15 is a perspective view of the fixation assembly 500, coupled to inferior strut 404. Fixation assembly 500 comprises a fixation member 502, a base 504, a top nut 506, a split ring clamp 508, a split sphere 510 and a set screw 512. Fixation assembly 500 may also be termed an attachment mechanism, and it is adjustable, permitting polyaxial rotation of the inferior strut relative to the fixation member 502.

Figure 16:
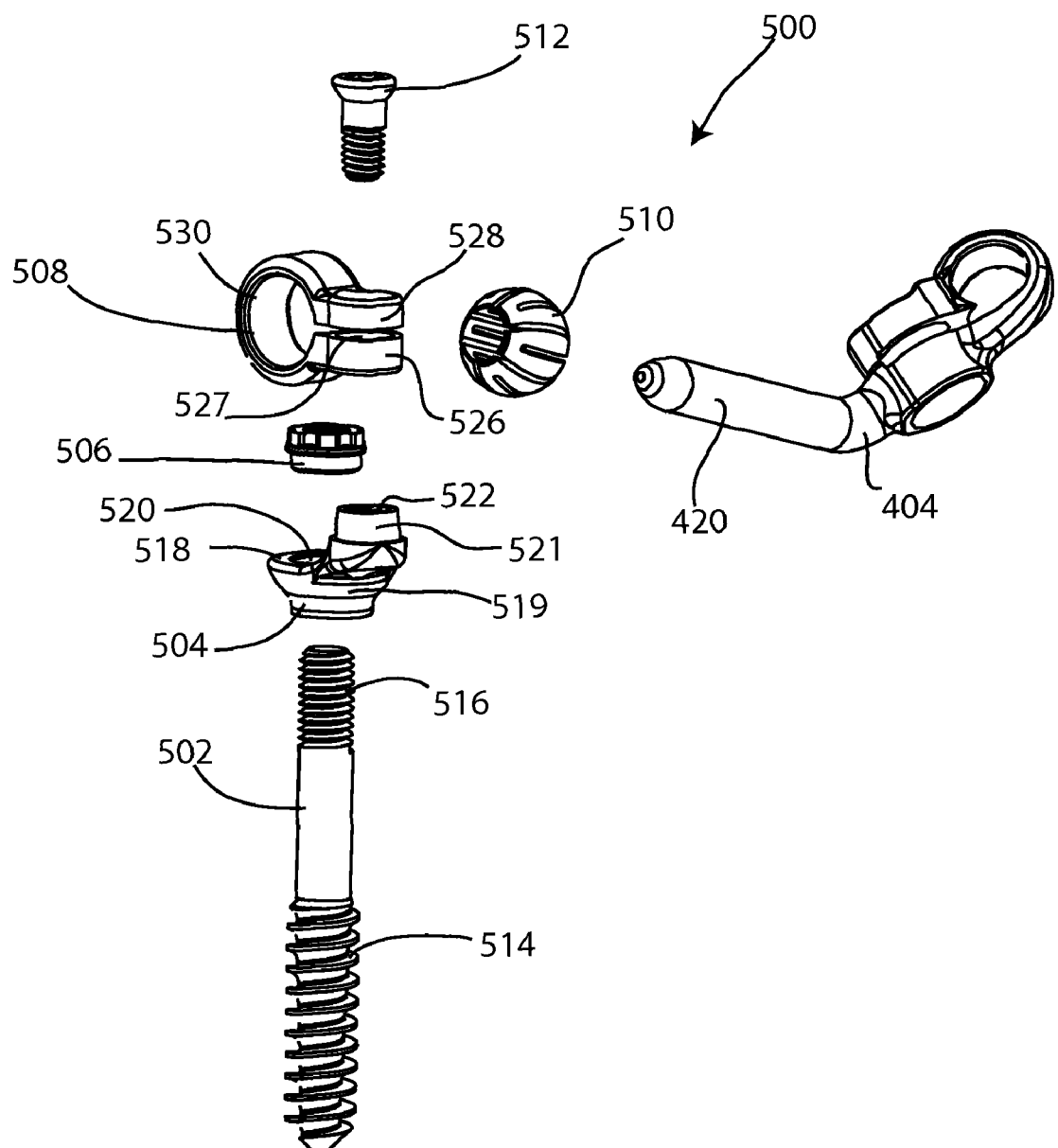
FIG. 16 is an exploded view of the fixation assembly and inferior strut of FIG. 15.

FIG. 16 is an exploded perspective view of the fixation assembly 500 and the inferior strut 404. The fixation member 502 comprises a threaded fixation portion 514 and a threaded attachment portion 516. The base 504 comprises a receptacle 518 with a fixation bore 520 sized to receive the fixation member 502, and a bone-facing side 519. On the bone-facing side 519 may be fins, pegs, teeth or other anti-rotation features. The base 504 may be dish-shaped as in FIG. 16, or may be spherical, tapered, or another shape. Coupled to the receptacle 518 is a tapered pedestal 521 which encircles a threaded attachment bore 522 sized to receive the set screw 512. The top nut 506 is sized to fit into the receptacle 518, and to be threaded onto the attachment portion 516 of the fixation member. The split ring clamp 508 comprises an inner ring 526, an outer ring 528, and a collar 530 which connects the inner and outer rings. An inner wall 527 of the inner ring 526 may be tapered. The set screw 512 is threaded and sized to be received in the attachment bore 522. The split sphere 510 is sized to fit around the rod-like first end 420 of the inferior strut 404, and sized to fit inside the collar 530 of the split ring clamp 508. A mirror-image fixation assembly 501 is configured to be implanted on the right side of the vertebra.

Returning to FIG. 15, fixation assembly 500 may be assembled and locked down as follows. Fixation member 502 is driven into a prepared pedicle at a desired depth. Base 504 is placed on the fixation member 502 so that the threaded attachment portion 516 fits through the fixation bore 520. The outer surface of the base 504 may rest on the prepared pedicle. The top nut is threaded onto the attachment portion 516 and actuated to secure the base 504 to the pedicle. The split sphere 510 is fitted into the collar 530 of the split ring clamp 508, and the rod portion 420 of the inferior strut may be slid into the split sphere. The split ring clamp 508, now connected to the inferior strut 404, is placed on the pedestal 521 so that the inner ring 526 surrounds the tapered pedestal 521. The set screw 512 is fit through the outer and inner rings 526, 528 and threaded into the attachment bore 522. At this junction the angle of the inferior strut 404 relative to a clamp axis 532, which may be parallel to the fixation member 502, may be adjusted. Also, the split sphere 510 may be polyaxially rotated within the collar 530, permitting polyaxial adjustment of the inferior strut 404. When the preferred orientation of the inferior strut 404 relative to the clamp axis 532, and the preferred orientation of the inferior strut to the collar 530 are reached, the fixation assembly 500 is locked down by actuating the set screw 512. As set screw 512 is tightened, outer ring 528 is urged toward inner ring 526. As the rings 526, 528 come together, collar 530 is compressed around split sphere 510, which in turn compresses around rod portion 420, locking its position. As set screw 512 is turned, the tapered inner wall 527 of inner ring 526 is rigidly secured against the tapered pedestal 521, fixing the position of the split clamp ring 508 relative to the clamp axis 532.

With reference to FIGS. 12-16, the components comprising the fixation assemblies 300, 500, 501, superior 210, 211 and inferior 400, 401 implants and crosslink 109 may be implanted as follows. The pedicles are prepared for implantation, which may include removal of natural facet surfaces and bone preparation, and may include a broaching step to shape the pedicles to receive the base components. Broaching may ensure bone ingrowth and better mechanical retention of the bases and therefore the full implant system. Initially the fixation member 302 for each fixation assembly 300 is driven into the caudal pedicles to a prescribed or desired depth. A tapered base 304 is placed on each fixation member 302. A split sphere 306 is placed on the tapered bases 304 intended for the superior implants, and the superior implants 210, 211 are placed over the split spheres, and the taper lock is locked down relative to the fixation assembly as described previously with reference to FIGS. 8-10

Before or after the fixation assemblies 300 are prepared, the fixation members 502 for the fixation assemblies 500, 501 are driven to a desired depth. On the left side, base 504 is placed over the fixation member 502 and secured by the top nut 506. The inferior strut 404 is assembled with the inferior articular body 402, and the attachment mechanisms 406 as set forth previously, but not locked down. The split ring clamp 508 is assembled with the split sphere 510, and together they are slid onto the inferior strut 404. The split ring clamp 508, now attached to the inferior strut 404 and the inferior implant 400, is placed on the tapered pedestal 521 of the base 504. On the right side, mirror-image duplicates of the left components are similarly assembled. The inferior implants 400, 401 are positioned so that the inferior articular surfaces are aligned with the superior articular surfaces, and the inferior and superior articular bodies on each side may be temporarily clipped together to maintain the alignment. The inferior implant/strut assemblies are locked down to the fixation assemblies by actuating the set screws 512.

The crosslink 109 may now be inserted through the collar 530 of the split clamp 508 of one inferior implant 400 or 401 and through a prepared spinous process, and through the other collar 530 on the remaining inferior implant 400 or 401. Alternatively, the crosslink 109 may be inserted before the inferior implants are locked down to the fixation assemblies. The attachment mechanisms 406 of each inferior implant 400, 401 are actuated to lock down the implants, fixing the positions of the articular surfaces 403, the inferior struts 404 and the crosslink 109.

Figure 17:
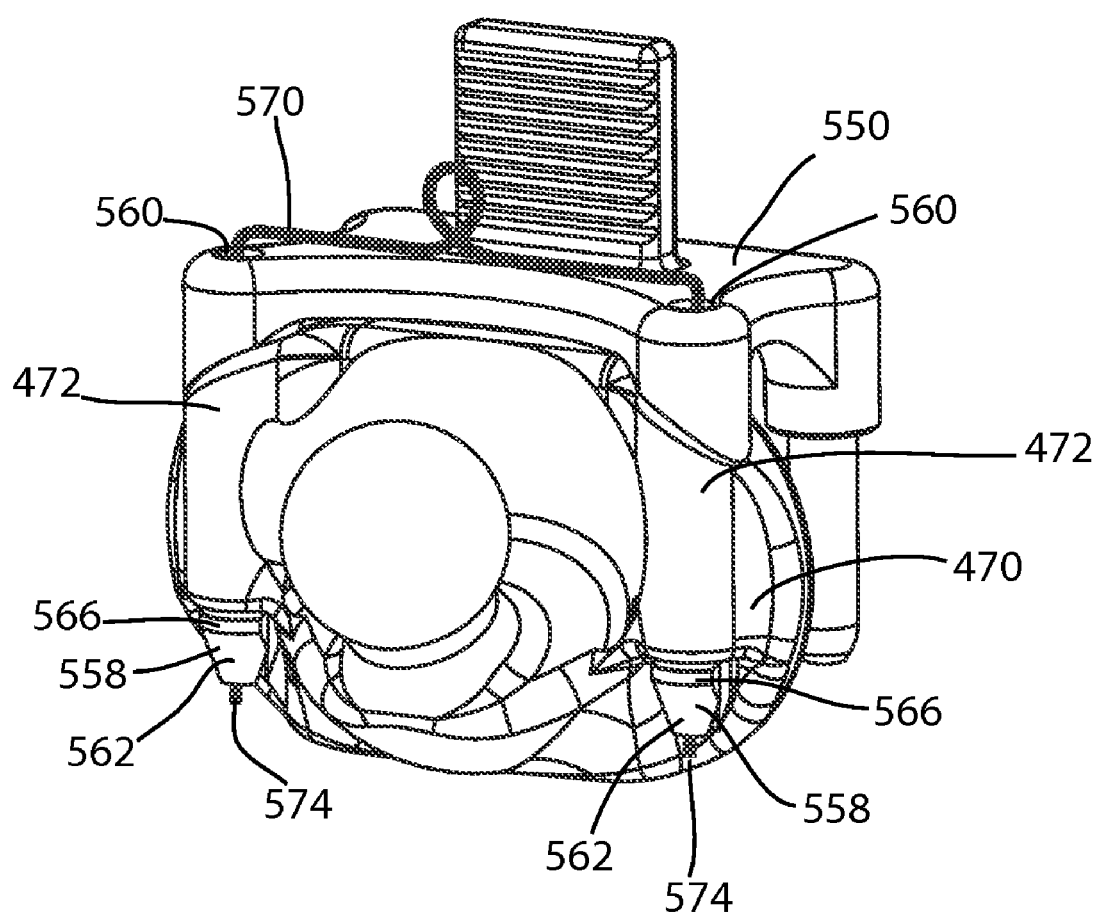
FIG. 17 is a perspective view of an inferior implant body coupled to a clip.

Some variation in the steps described above may occur. For example, as seen in FIG. 17, an inferior articular body 470 may be available pre-packaged temporarily attached to a clip 550 with a plug 570, which will be described in further detail below. Alternatively, a gripping tool (not shown) may be used to hold the inferior articular body 470. The attachment mechanism 406 and the inferior strut 404 (not seen) are assembled to the inferior articular body 470. The superior implant 210 is placed on and taper locked with the fixation assembly 300, which is implanted in the pedicle. Using the clip 550 or gripping tool as a handle, the inferior implant articular body 470 with attached strut is placed adjacent to implanted superior implant 210 such that pins on the clip 550 engage in openings on the superior implant, and the inferior and superior articulation surfaces are aligned. Then the inferior strut 404 is slid into the split sphere 510 and the split ring clamp 508 of the fixation assembly 500. (Alternatively, the split sphere and split ring clamp 530 may be assembled to the inferior strut 404 before it is placed adjacent to the superior implant). Polyaxiality of the split sphere 510 relative to the collar 530 may be adjusted, and the set screw 512 is inserted and the fixation assembly 500 is locked down. The insertion of the crosslink 109 and final adjustment and lockdown of attachment mechanism 406 is as described previously. The clip 550 is removed.

Figure 18A:
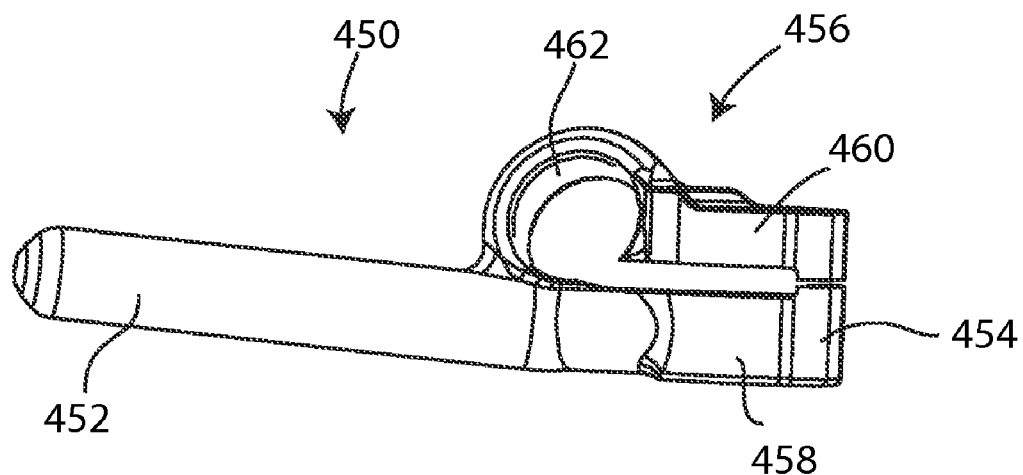
FIG. 18A is a perspective view of an alternate inferior strut.
Figure 18:
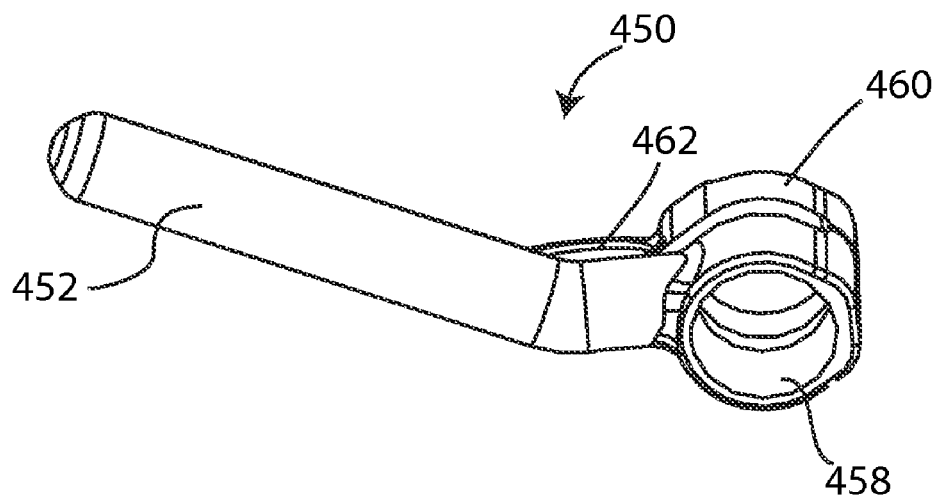
FIG. 18B is a perspective view from an alternate angle of the strut of FIG. 18A.

FIGS. 18A and 18B depict different perspective views of an alternate inferior strut 450. Inferior strut comprises a first end 452 and a second end 454. First end 452 is post-like, and may be configured to be secured by a fixation assembly such as fixation assembly 500 seen in FIG. 15. The second end 454 comprises a split ring clamp 456, which includes an inner ring 458 and an outer ring 460, which are joined by a collar portion 462. As seen in FIGS. 18A and 18B, the collar portion may be substantially orthogonal relative to the rings 458, 460, or it may be at another angle. Additionally, the angle of the second end 454 relative to the first end 452 may vary. Inferior strut 450 may be secured to an articular body by an attachment mechanism in the same manner as described for inferior strut 404; that is, a single actuating member may be actuated to urge the inner and outer rings 458, 460 together and compress the collar 462. Inferior strut 450 may differ from inferior strut 404 in features such as the position and/or angle of the split rings relative to the collar, and the angle of the second end comprising the split ring clamp relative to axis of the first post-like end, among others. It is appreciated that any inferior strut disclosed herein may be available in a variety of lengths, sizes, angles, and split ring clamp configurations.

Another alternative inferior strut (not pictured) may include separate polyaxially adjustable attachment mechanisms for a crosslink and an inferior articular body. Such an alternative strut may include a first ring positioned and shaped to receive a polyaxially adjustable crosslink rod, while a second ring is positioned and shaped to receive a polyaxially adjustable connection to an inferior articular body. Each ring may have an independent lockout mechanism such as a nut or screw.

Figure 19:
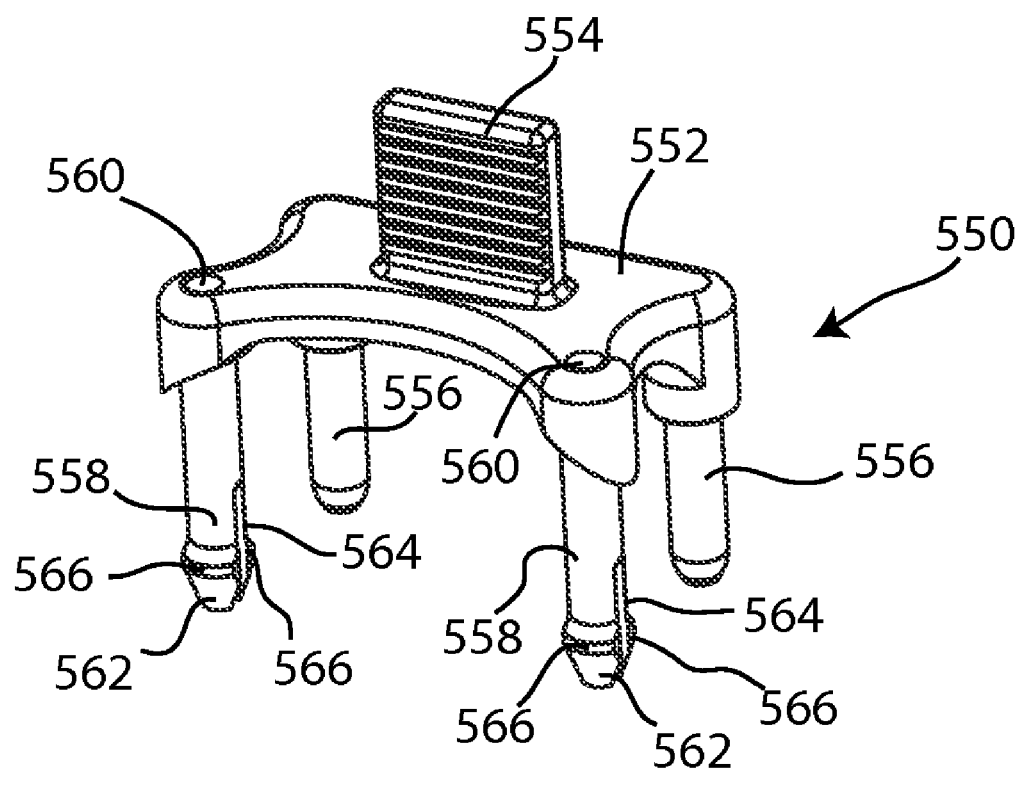
FIG. 19 is a perspective view of the clip of FIG. 17 and a plug.
Figure 19:
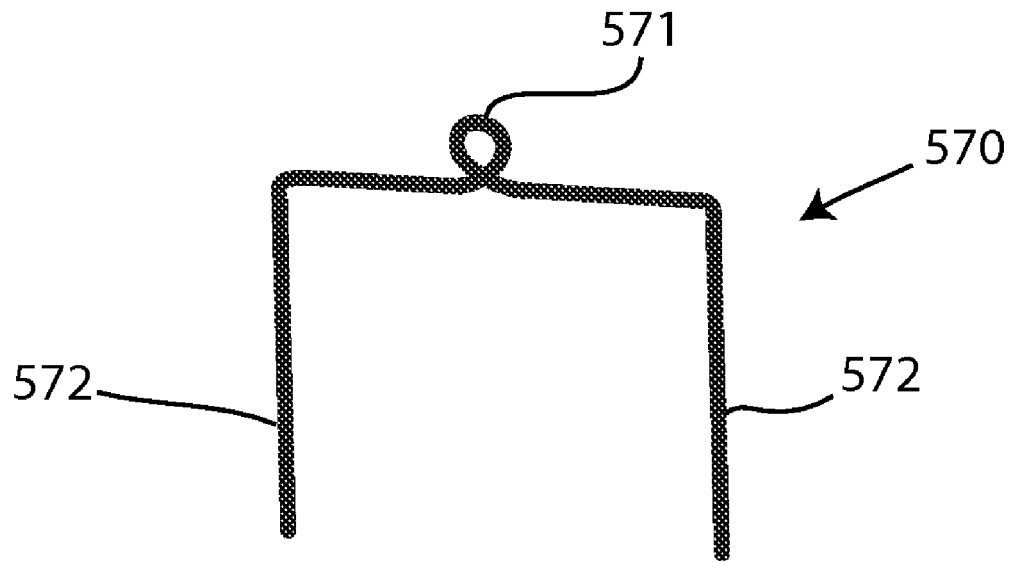

FIG. 19 is a perspective view of the clip 550 and the plug 570. Clip 550 comprises a clip body 552, a handle 554, and two pairs of pins which extend substantially orthogonally from the body: a pair of superior pins 556 and a pair of inferior pins 558. The inferior pins 558 are cannulated, each having a bore 560 which extends the length of the pin, from the body 552 to a split end 562. Each split end 562 includes at least one slot 564 which extends partially along the length of the pin 558, and a protruding flange 566.

The plug 570 comprises a handle 572 and two prongs 574 which are sized to extend through the bores 560 of the inferior pins 558 of the clip 550. When the plug 570 is inserted fully into the inferior pins 558, the prongs 574 urge apart the split ends 562 from a narrow first configuration to an expanded second configuration in which the slots 564 are widened, and the flanges 566 on each pin are farther apart. When the plug 570 is removed, the split ends 562 return from the expanded second configuration to the narrow first configuration.

Returning to FIG. 17, the inferior articular body 470 is shown coupled with the clip 550 and the plug 570. The inferior pins 558 extend through tubes 472 formed on the inferior implant 470, such that the split ends 562 and flanges 566 emerge outside of the tubes. The plug 570 is fully inserted through the clip bores 560, and therefore the prongs 574 keep the split ends in the expanded second configuration. In the expanded second configuration, the widened flanges 566 cause the diameter of the split ends 562 to be greater than the diameter of the tubes 472, preventing the clip 570 from being withdrawn from the inferior articular body 470. Thus held by the clip 550, the inferior articular body 470, with or without other attached components such as an inferior strut, may be clipped to a superior implant.

Figure 20:
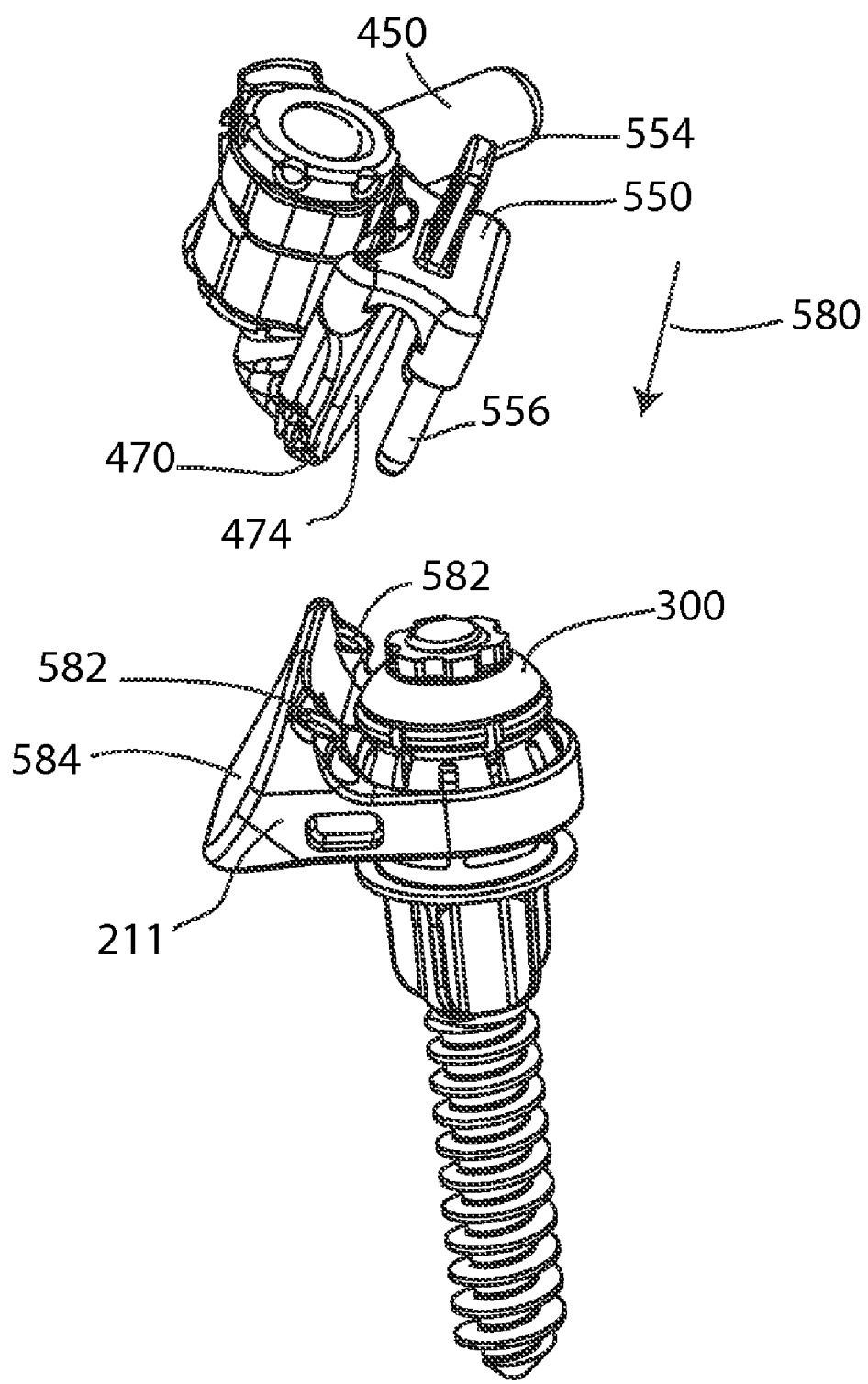
FIG. 20 is a perspective view of the clip of FIG. 17 coupled to an inferior facet joint implant, and the superior facet joint implant and fixation assembly of FIG. 8.

Referring to FIG. 20, a perspective view shows the inferior articular body 470 joined to an inferior strut 450, attached to a clip 550. A direction arrow 580 indicates the direction in which the articular body, strut and clip may moved to align them with a superior implant 211. For viewing clarity, no bone is shown, but the superior implant 211 may be implanted in a pedicle via fixation member 300 previous to alignment with the inferior articular body 470. Using the handle 554, the clip may be moved until the superior pins 556 fit into openings 582 on the superior implant 211.

Figure 21:
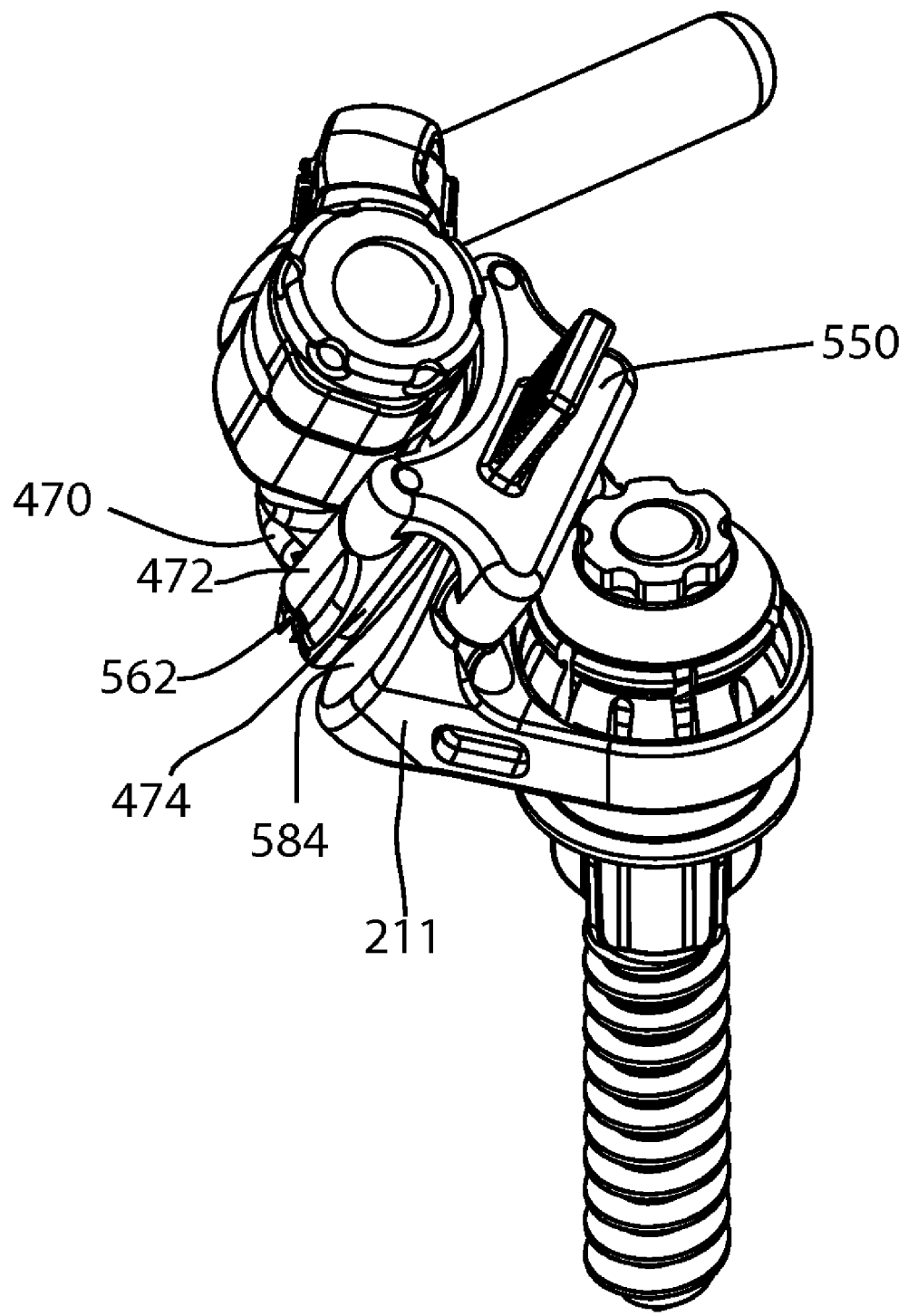
FIG. 21 is a perspective view of the inferior and superior facet joint implants of FIG. 20 joined by the clip of FIG. 17.

As seen in FIG. 21, when the pins 556 are fully inserted into the openings 582, inferior articulation surface 474 is aligned with superior articulation surface 584 in a preferred orientation. At this point, the orientation of the inferior strut may be adjusted, and locked down to a fixation member. Additionally, a crosslink rod may be added and locked down as the attachment mechanism is locked down. To remove the clip 550, first the plug 570 is removed, allowing the split ends 562 to return to the first narrow configuration and making them narrow enough to be withdrawn through the tubes 472. Then the clip 550 may be removed.

Figure 22:
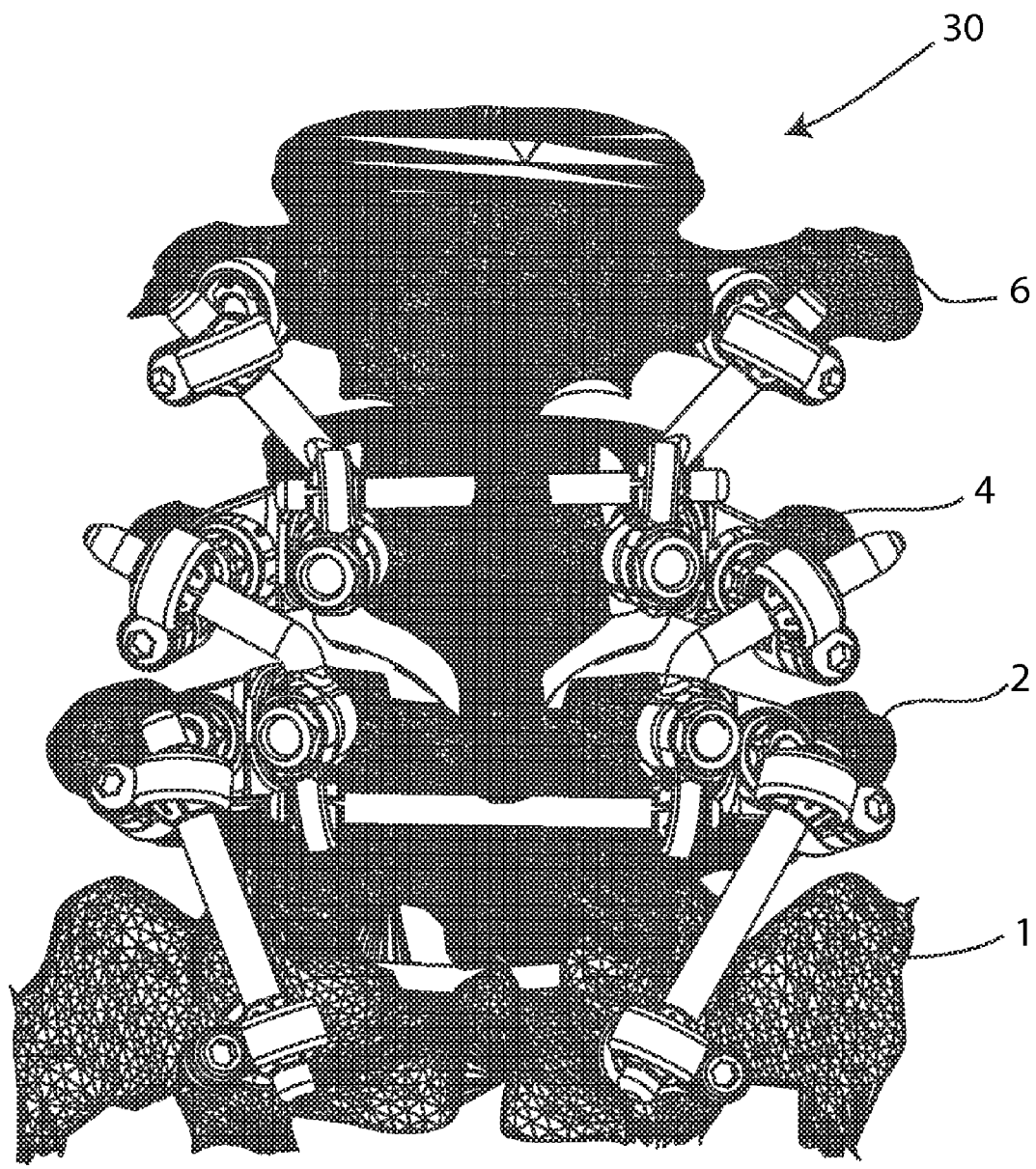
FIG. 22 is a perspective view of a multi-level facet joint replacement system implanted in a portion of a spine.

Referring to FIG. 22, a multi-level facet joint replacement system 30 is shown implanted in a portion of a spine. Between adjacent vertebrae 6 and 4, a first artificial facet joint replacement assembly replaces the natural facet joints. The first assembly is linked to a second artificial facet joint replacement assembly which replaces the natural facet joints between adjacent vertebrae 4 and 2. At the next level, the second artificial facet joint replacement assembly is linked to a fusion rod system which provides rigid fusion between vertebra 2 and the sacrum 1. Crosslink rods connect the left lateral assemblies with the right lateral assemblies.

Figure 23:
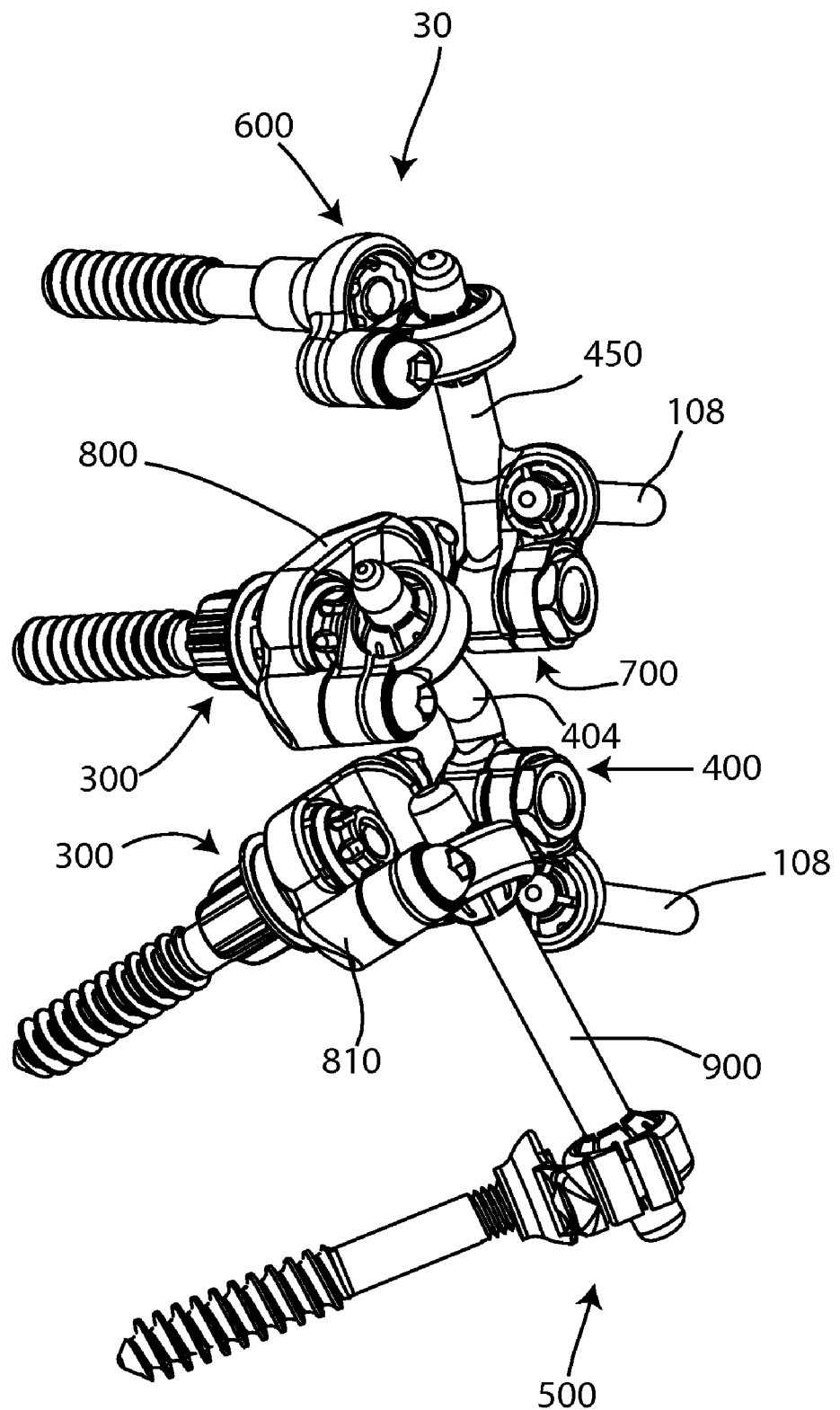
FIG. 23 is a lateral perspective view of a portion of the multi-level facet joint replacement system of FIG. 22.

Referring to FIG. 23, a lateral view shows the left lateral side of system 30. System 30 comprises many of the same components as system 20. Viewing the system in a cephalad to caudal direction, system 30 includes a fixation assembly 600 configured to be implanted in a first vertebra. An inferior strut 450 is secured by a split clamp to fixation assembly 600, and forms part of inferior facet implant 700. Inferior facet implant 700 articulates with a first superior facet implant 800 which is secured to a first fixation assembly 300 which is configured to be implanted a second vertebra. An inferior strut 404 is secured by a split clamp to the first superior facet implant 800, and forms part of inferior facet implant 400. Inferior facet implant 400 articulates with a second superior facet implant 810 which is secured to a second fixation assembly 300 which is configured to be implanted in a third vertebra. A fusion rod 900 is secured by a split clamp to the second fixation assembly 300, and extends to a fourth vertebra or sacrum, where it is configured to be secured by a fixation assembly 500. Two crosslinks 108 are coupled to the inferior implants and extend across the sagittal plane to the right lateral side of the spine. Multi-level applications of this system are not restricted to three or four levels; additional vertebral levels could be included by adding additional components including inferior implants, superior implants, crosslinks, and/or fusion rods. It is appreciated that the sizes and configurations of components included in system 30 may vary to fit various vertebral sizes and configurations and particular patient anatomy The present invention includes variances of the system herein described. Alternative embodiments may include different geometries and intermediate parts. Changes in the geometry, especially on the ends of the inferior strut, could be made to facilitate instrumentation or overall function. Applications of the present invention may include single- or multi-level facet joint replacement, or other iterations in which a rod or rod-like member is fixed to a second member to attain spinal fusion.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for replacing at least a portion of a natural facet joint that controls motion between a first vertebra and a second vertebra, the system comprising:
   a fixation member implantable in a pedicle of the second vertebra; and
   an inferior facet joint implant comprising:
      an inferior articular surface shaped to replace a natural inferior articular surface of the second vertebra;
      an inferior strut comprising a first end and a second end, wherein the first end is securable to the fixation member; and
      an attachment mechanism comprising an adjustable configuration in which the inferior articular surface is connected to the second end in such a manner that permits relative rotation between the inferior articular surface and the second end about three orthogonal axes, and a locked configuration in which the inferior articular surface is rigidly secured to the second end, wherein the attachment mechanism further comprises an expandable member and a nut configured to urge expansion of the expandable member, wherein the attachment mechanism and inferior strut are simultaneously locked by actuating the nut.

2. The system of claim 1, wherein the first end comprises a post adjustably securable to the fixation member through the use of a second attachment mechanism coupled to the fixation member.

3. The system of claim 1, wherein the first end comprises a ring adjustably securable to the fixation member through the use of a second attachment mechanism coupled to the fixation member.

4. The system of claim 1, wherein the second end comprises a ring, wherein the attachment mechanism comprises:
   a compressible member positionable at least partially within the ring; and
   a locking member configured to be actuated relative to the compressible member to urge compression of the compressible member;
   wherein, in response to compression of the compressible member, an interior wall of a cavity of the compressible member exerts force against a rounded surface fixedly connected to the inferior articular surface to restrict rotation of the inferior articular surface relative to the ring to provide the locked configuration.

5. The system of claim 4, wherein the compressible member comprises a conical portion and a threaded post, wherein the locking member comprises a nut configured to threadably engage the threaded post such that tightening of the nut on the threaded post urges the conical portion through the ring to cause compression of the conical portion.

6. The system of claim 1, wherein the second end comprises a post, wherein the attachment mechanism and
   wherein, in response to expansion of the expandable member, a perimeter of the expandable member exerts force against an interior surface of the cavity to restrict rotation of the expandable member relative to the inferior articular surface to provide the locked configuration.

7. The system of claim 6, wherein the locking member comprises a conical expander and a threaded post and the attachment mechanism further comprises a nut configured to threadably engage the threaded post such that tightening of the nut on the threaded post draws the conical expander through an interior of the expandable member to urge expansion of the expandable member.

8. The system of claim 1, wherein the attachment mechanism, in the adjustable configuration, further permits relative translation between the inferior articular surface and the second end along at least one axis.

9. The system of claim 1, wherein the second end comprises a crosslink receiver connectable to a crosslink crossing a sagittal plane of the first and second vertebrae, wherein when the attachment mechanism, in the adjustable configuration, permits adjustment of the relative orientation independently of an orientation of the crosslink.

10. A system for replacing at least a portion of a natural facet joint that controls motion between a first vertebra and a second vertebra, the system comprising:
    a fixation member implantable in a pedicle of the second vertebra; and
    an inferior facet joint implant comprising:
    an inferior articular surface shaped to replace a natural inferior articular surface of the second vertebra;
    an inferior strut comprising a first end and a second end, wherein the first end is securable to the fixation member and the second end comprises a crosslink receiver connectable to a crosslink crossing a sagittal plane of the first and second vertebrae; and
    an attachment mechanism comprising an adjustable configuration in which the inferior articular surface is adjustably connected to the second end independently of an orientation of the crosslink, and a locked configuration in which the inferior articular surface is rigidly secured to the second end, wherein the attachment mechanism further comprises an expandable member and a nut configured to urge expansion of the expandable member, wherein the attachment mechanism and inferior strut are simultaneously locked by actuating the nut.

11. The system of claim 10, wherein the first end comprises a post adjustably securable to the fixation member through the use of a second attachment mechanism coupled to the fixation member.

12. The system of claim 10, wherein the first end comprises a ring adjustably securable to the fixation member through the use of a second attachment mechanism coupled to the fixation member.

13. The system of claim 10, wherein the second end comprises a ring, wherein the attachment mechanism comprises:
    a compressible member positionable at least partially within the ring; and
    a locking member configured to be actuated relative to the compressible member to urge compression of the compressible member;
    wherein, in response to compression of the compressible member, an interior wall of a cavity of the compressible member exerts force against a rounded surface fixedly connected to the inferior articular surface to restrict rotation of the inferior articular surface relative to the ring to provide the locked configuration.

14. The system of claim 13, wherein the compressible member comprises a conical portion and a threaded post, wherein the locking member comprises a nut configured to threadably engage the threaded post such that tightening of the nut on the threaded post urges the conical portion through the ring to cause compression of the conical portion.

15. The system of claim 10, wherein the second end comprises a post, wherein the attachment mechanism comprises:
    an expandable member positionable at least partially within a cavity proximate the inferior articular surface; and
    a locking member configured to be actuated relative to the expandable member to urge expansion of the expandable member;
    wherein, in response to expansion of the expandable member, a perimeter of the expandable member exerts force against an interior surface of the cavity to restrict rotation of the expandable member relative to the inferior articular surface to provide the locked configuration.

16. The system of claim 15, wherein the locking member comprises a conical expander and a threaded post and the attachment mechanism further comprises a nut configured to threadably engage the threaded post such that tightening of the nut on the threaded post draws the conical expander through an interior of the expandable member to urge expansion of the expandable member.

17. The system of claim 10, wherein the crosslink receiver comprises a collar through which the crosslink is insertable, the system further comprising a second attachment mechanism configured to secure the collar to the crosslink at any of a plurality of relative orientations between the collar and the crosslink about at least two orthogonal axes.

18. A system for replacing at least a portion of a natural facet joint that controls motion between a first vertebra and a second vertebra, the system comprising:
    a left fixation member implantable in a left pedicle of the second vertebra;
    a right fixation member implantable in a right pedicle of the second vertebra;
    a left inferior facet joint implant comprising:
    a left inferior articular surface shaped to replace a natural left inferior articular surface of the second vertebra;

a left inferior strut comprising a first end and a second end, wherein the first end is securable to the fixation member; and
a left attachment mechanism; and
a right inferior facet joint implant comprising:
a right inferior articular surface shaped to replace a natural right inferior articular surface of the second vertebra;
a left inferior strut comprising a first end and a second end, wherein the first end is securable to the right fixation member; and
a right attachment mechanism;
wherein each attachment mechanism comprises an adjustable configuration in which the corresponding inferior articular surface is connected to the corresponding second end in such a manner that permits relative rotation between the corresponding inferior articular surface and the corresponding second end about three orthogonal axes, and a locked configuration in which the corresponding inferior articular surface is rigidly secured to the corresponding second end, wherein each attachment mechanism further comprises an expandable member and a nut configured to urge expansion of the expandable member, wherein each attachment mechanism and their respective strut are simultaneously locked by actuating a nut.

19. The system of claim 18, wherein each second end comprises a ring, wherein each attachment mechanism comprises:
a compressible member positionable at least partially within the ring; and
a locking member configured to be actuated relative to the compressible member to urge compression of the compressible member;
wherein, in response to compression of the compressible member, an interior wall of a cavity of the compressible member exerts force against a rounded surface fixedly connected to the inferior articular surface to restrict rotation of the inferior articular surface relative to the ring to provide the locked configuration;
wherein the compressible member comprises a conical portion and a threaded post, wherein the locking member comprises a nut configured to threadably engage the threaded post such that tightening of the nut on the threaded post urges the conical portion through the ring to cause compression of the conical portion
wherein each of the first ends comprises a post adjustably securable to the corresponding fixation member.

20. The system of claim 19, wherein each second end comprises a post, wherein each attachment mechanism comprises:
an expandable member positionable at least partially within a cavity proximate the inferior articular surface; and
a locking member configured to be actuated relative to the expandable member to urge expansion of the expandable member;
wherein, in response to expansion of the expandable member, a perimeter of the expandable member exerts force against an interior surface of the cavity to restrict rotation of the expandable member relative to the inferior articular surface to provide the locked configuration;
wherein the locking member comprises a conical expander and a threaded post and the attachment mechanism further comprises a nut configured to threadably engage the threaded post such that tightening of the nut on the threaded post draws the conical expander through an interior of the expandable member to urge expansion of the expandable member;
wherein each of the first ends comprises a ring adjustably securable to the corresponding fixation member.

21. The system of claim 19, further comprising:
a left superior facet joint implant securable to a left pedicle of the first vertebra, the left superior facet joint implant comprising a left superior articular surface;
a right superior facet joint implant securable to a right pedicle of the first vertebra, the right superior facet joint implant comprising a right superior articular surface;
wherein, when all of the facet joint implants are secured to the corresponding pedicles, the left superior articular surface is positioned to articulate with the left inferior articular surface and the right superior articular surface is positioned to articulate with the right inferior articular surface.

* * * * *